United States Patent
Park et al.

(10) Patent No.: US 11,649,472 B2
(45) Date of Patent: May 16, 2023

(54) CONTROLLING METABOLISM BY SUBSTRATE COFEEDING

(71) Applicant: Massachusetts Institute of Technology, Cambridge, MA (US)

(72) Inventors: Junyoung Park, Cambridge, MA (US); Nian Liu, Cambridge, MA (US); Gregory Stephanopoulos, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 14 days.

(21) Appl. No.: 16/023,336

(22) Filed: Jun. 29, 2018

(65) Prior Publication Data

US 2019/0032003 A1 Jan. 31, 2019

Related U.S. Application Data

(60) Provisional application No. 62/527,630, filed on Jun. 30, 2017.

(51) Int. Cl.

| | | |
|---|---|---|
| *C12P 7/54* | (2006.01) | |
| *C12P 7/6409* | (2022.01) | |
| *C12P 7/6463* | (2022.01) | |
| *C12N 1/20* | (2006.01) | |
| *C12N 1/16* | (2006.01) | |
| *C12N 1/32* | (2006.01) | |
| *C12N 9/22* | (2006.01) | |
| *C12N 9/42* | (2006.01) | |
| *C12N 9/26* | (2006.01) | |
| *C12P 7/64* | (2022.01) | |
| *C12R 1/02* | (2006.01) | |
| *C12R 1/145* | (2006.01) | |

(52) U.S. Cl.
CPC .................. *C12P 7/54* (2013.01); *C12N 1/16* (2013.01); *C12N 1/205* (2021.05); *C12N 1/32* (2013.01); *C12N 9/22* (2013.01); *C12N 9/2437* (2013.01); *C12N 9/2474* (2013.01); *C12P 7/64* (2013.01); *C12P 7/6409* (2013.01); *C12P 7/6463* (2013.01); *C12R 2001/02* (2021.05); *C12R 2001/145* (2021.05); *C12Y 302/01004* (2013.01); *C12Y 302/01035* (2013.01)

(58) Field of Classification Search
CPC ... C12N 1/16; C12N 1/32; C12N 9/22; C12N 9/2437; C12N 9/2474; C12N 1/205; C12P 7/6409; C12P 7/6463; C12P 7/64; C12P 7/54; C12R 1/02; C12R 1/145; C12R 2001/02; C12R 2001/145; C12Y 302/01004; C12Y 302/01035
See application file for complete search history.

(56) References Cited

U.S. PATENT DOCUMENTS

| | | |
|---|---|---|
| 6,509,180 B1 | 1/2003 | Verser et al. |
| 6,870,004 B1 | 3/2005 | Nguyen et al. |
| 8,440,729 B2 | 5/2013 | Olah et al. |
| 8,592,633 B2 | 11/2013 | Cole et al. |
| 9,175,408 B2 | 11/2015 | Lovley et al. |
| 2011/0177564 A1* | 7/2011 | Stephanopoulos ....... C12P 7/16 435/101 |
| 2015/0125912 A1* | 5/2015 | Haas ......................... C12P 7/62 435/134 |
| 2015/0252483 A1 | 9/2015 | Ono et al. |
| 2015/0284747 A1* | 10/2015 | Schiemann ............... C12P 7/16 435/141 |
| 2016/0251683 A1 | 9/2016 | Tracy et al. |

FOREIGN PATENT DOCUMENTS

WO    WO 2013/181647 A2    12/2013

OTHER PUBLICATIONS

Jones, SW et la. CO2 fixation by anaerobic non-photosynthetic mixotrophy for improved carbon conversion. Nature Communications. 2016. 7:12800. 9 pages. Published Sep. 30, 2016. (Year: 2016).*
Gerson, DF et al. Substrate concentration control in bioreactors. Biotechnology and Genetic Engineering Reviews. 1988. 6(1): 67-150. (Year: 1988).*
Godley, AR et al. The effect of carbon dioxide on the growth kinetics of fructose-limited chemostat cultures of Acetobacterium woodii DSM 1030. Arch. Microbiol. 1990. 154: 5-11. (Year: 1990).*
Peters, V et al. Efficiency of hydrogen utilization during unitrophic and mixotrophic growth of Acetobacterium woodii on hydrogen and lactate in the chemostat. FEMS Microbiology Ecology. 1998. 26: 317-324. (Year: 1998).*
Li, T et al. Open and continuous fermentation: Products, conditions and bioprocess economy. Biotechnology Journal. 2014. 9: 1503-1511. (Year: 2014).*
Schuchmann, K et al. Energetics and application of heterotrophy in acetogenic bacteria. Applied and Environmental Microbiology. 2016. 82(14): 4056-4069. Published Jun. 30, 2016. (Year: 2016).*
Beisel, CL et al. Rethinking the hierarchy of sugar utilization in bacteria. Journal of Bacteriology. 2016. 198(3): 374-376. Published Jan. 15, 2016. (Year: 2016).*

(Continued)

*Primary Examiner* — Renee Claytor
*Assistant Examiner* — Susan E. Fernandez
(74) *Attorney, Agent, or Firm* — Wolf, Greenfield & Sacks, P.C.

(57) ABSTRACT

The disclosure provides methods using mixed substrate cofeeding for bioproduct synthesis, which enables faster, more efficient, and higher yield carbon conversion in various organisms.

18 Claims, 13 Drawing Sheets

(56) References Cited

OTHER PUBLICATIONS

Kopke, M et al. Clostridium ljungdahlii represents a microbial production platform based on syngas. PNAS. 2010. 107(29): 13087-13092. (Year: 2010).*

Berzin et al., Selective production of acetone during continuous synthesis gas fermentation by engineered biocatalyst *Clostridium* sp. MAceT113. Lett Appl Microbiol. Aug. 2012;55(2):149-54. doi: 10.1111/j.1472-765X.2012.03272.x. Epub Jun. 15, 2012.

Martin et al., Dissimilation of carbon monoxide to acetic acid by glucose-limited cultures of Clostridium thermoaceticum. Appl Environ Microbiol. Jun. 1985;49(6):1412-7.

Sakai et al., Acetate and ethanol production from H2 and CO2 by *Moorella* sp. using a repeated batch culture. J Biosci Bioeng. Mar. 2005;99(3):252-8.

Antoniewicz et al., Determination of confidence intervals of metabolic fluxes estimated from stable isotope measurements. Metab Eng. Jul. 2006;8(4):324-37. doi: 10.1016/j.ymben.2006.01.004. Epub Apr. 24, 2006.

Antoniewicz et al., Elementary metabolite units (EMU): A novel framework for modeling isotopic distributions. Metab Eng. Jan. 2007;9(1):68-86. Epub Sep. 17, 2006.

Aristilde et al., Hierarchy in Pentose Sugar Metabolism in Clostridium Acetobutylicum. Appl Environ Microbiol. Dec. 19, 2014;81(4):1452-62. Epub Jan. 30, 2015. doi: 10.1128/AEM.03199-14.

Atsumi et al., Non-fermentative pathways for synthesis of branched-chain higher alcohols as biofuels. Natur. Jan. 3, 2008;451(7174):86-9. doi: 10.1038/nature06450.

Blazeck et al., Harnessing Yarrowia lipolytica lipogenesis to create a platform for lipid and biofuel production. Nat Commun. Jan. 20, 2014;5:3131.

Bren et al., Glucose becomes one of the worst carbon sources for *E.coli* on poor nitrogen sources due to suboptimal levels of cAMP. Sci Rep. Apr. 25, 2016;6:24834, 10 pages.

Casazza et al., The Interdependence of Glycolytic and Pentose Cycle Intermediates in Ad-Libitum Fed Rats. J Biol Chem. Jan. 15, 1986;261(2):690-8.

Clasquin et al., LC-MS data processing with MAVEN: a metabolomic analysis and visualization engine. Curr Protoc Bioinformatics. Mar. 2012;0 14:Unit14. 31 pages.

Daniel et al., Characterization of the H2- and CO-dependent chemolithotrophic potentials of the acetogens Clostridium thermoaceticum and Acetogenium kivui. J Bacteriol. Aug. 1990;17298):4464-71.

Daniell et al., Commercial biomass syngas fermentation. Energies. Dec. 19, 2012;5(12):5372-417.

Gancedo, Carbon catabolite repression in yeast. Eur J Biochem. Jun. 1992;206(2):297-313. doi: 10.1111/j.1432-1033.1992.tb16928.x.

Goerke et al., Carbon catabolite repression in bacteria: many ways to make the most out of nutrients. Nat Rev Microbiol. Aug. 2008;6(8):613-24. doi: 10.1038/nrmicro1932.

Haynes et al., Rethinking biological activation of methane and conversion to liquid fuels. Nat Chem Biol. May 2014;10(5):331-9.

Hermsen et al., A growth-rate composition formula for the growth of *E.coli* on co-utilized carbon substrates. Mol Syst Biol. Apr. 9, 2015;11(4):801.

Hu et al., Anaerobic CO2 fixation by the acetogenic bacterium *Moorella thermoacetica*. AIChE J. Apr. 23, 2013;59(9):3176-83.

Islam et al., Investigating Moorella thermoacetica metabolism with a genome-scale constraint-based metabolic model. Integr Biol (Camb). Aug. 2015;7(8):869-82.

Joshua et al., Absence of diauxie during simultaneous utilization of glucose and Xylose by Sulfolobus acidocaldarius. J Bacteriol. Mar. 2011;193(6):1293-301.

Kim et al., Simultaneous utilization of glucose and xylose via novel mechanisms in engineered *Escherichia coli*. Metab Eng. Jul. 2015;30:141-8.

Kita et al., Development of genetic transformation and heterologous expression system in carboxydotrophic thermophilic acetogen Moorella thermoacetica. J Biosci Bioeng. Apr. 2013;115(4):347-52.

Ledesma-Amaro et al., Combining metabolic engineering and process optimization to improve production and secretion of fatty acids. Metab Eng. Nov. 2016;38:38-46.

Ledesma-Amaro et al., Metabolic Engineering for Expanding the Substrate Range of Yarrowia lipolytica. Trends Biotechnol. Oct. 2016;34(10):798-809.

Mall et al., Reversibility of citrate synthase allows autotrophic growth of a thermophilic bacterium. Science. Feb. 2, 2018;359(6375):563-7.

Martin et al., Engineering a mevalonate pathway in *Escherichia coli* for production of terpenoids. Nat. Biotechnol. Jun. 1, 2003;21:796-802.

Martinez et al., Coutilization of glucose and glycerol enhances the production of aromatic compounds in an *Escherichia coli* strain lacking the phosphoenolpyruvate: carbohydrate phosphotransferase system. Microb Cell Fact. Jan. 22, 2008;7:1, 12 pages.

Michaelis et al., Oxidation-reduction systems of biological significance. II. Reducing effect of cysteine induced by free metals. J Biol Chem. Jan. 1929;81:29-40.

Muller, Energy conservation in acetogenic bacteria. Appl Environ Microbiol. Nov. 2003;69(11):6345-53.

Naik et al., Production of first and second generation biofuels: A comprehensive review. Ren Sust Energy Rev. Feb. 2010;14(2):578-97.

Nunoura et al., A primordial and reversible TCA cycle in a facultatively chemolithoautotrophic thermophile. Science. Feb. 2, 2018;359(6375):559-63.

Qiao et al., Engineering lipid overproduction in the oleaginous yeast *Yarrowia lipolytica*. Metab Eng. May 2015;29:56-65.

Qiao et al., Lipid production in Yarrowia lipolytica is maximized by engineering cytosolic redox metabolism. Nat Biotechnol. Feb. 2017;35(2): 173-7.

Rabinowitz et al., Acidic acetonitrile for cellular metabolome extraction from *Escherichia coli*. Anal Chem. Aug. 15, 2007;79(16):6167-73.

Ragsdale et al., Acetogenesis and the Wood-Ljungdahl pathway of CO2 fixation. Biochim Biophys Acta. Dec. 2008;1784(12):1873-98.

Ratledge et al., The biochemistry and molecular biology of lipid accumulation in oleaginous microorganisms. Adv Appl Microbiol. 2002;51:1-51. doi: 10.1016/s0065-2164(02)51000-5.

Raymond, The Evolution of Biological Carbon and Nitrogen Cycling—a Genomic Perspective. Reviews Mineralogy Geochemistry. Jan. 1, 2005;59(1):211-31.

Sanchez et al., Improved xylose and arabinose utilization by an industrial recombinant *Saccharomyces cerevisiae* strain using evolutionary engineering. Biotechnol Biofuels. Jun. 15, 2010;3:13, 11 pages.

Schellenberger et al., Quantitative prediction of cellular metabolism with constraint-based models: the COBRA Toolbox v2.0. Nat Protoc. Sep. 1, 2011;6(9):1290-1307. Epub Aug. 4, 2011.

Schuchmann et al., Autotrophy at the thermodynamic limit of life: a model for energy conservation in acetogenic bacteria. Nat Rev Microbiol. Dec. 2014;12(12):809-21.

Tai et al., Engineering the push and pull of lipid biosynthesis in oleaginous yeast *Yarrowia lipolytica* for biofuel production. Metab Eng. Jan. 2013;15:1-19.

Tracy et al., Clostridia: the importance of their exceptional substrate and metabolite diversity for biofuel and biorefinery applications. Curr Opin Biotech. Jun. 2012;23:364-81.

Xu et al., Application of metabolic controls for the maximization of lipid production in semicontinuous fermentation. Proc Natl Acad Sci USA. Jul. 3, 2017;114:E5308.

Xue et al., Production of omega-3 eicosapentaenoic acid by metabolic engineering of Yarrowia lipolytica. Nat Biotechnol. Aug. 2013;31(8):734-40.

* cited by examiner

Oxaloacetate + Pyruvate ⟶ Lysine + $CO_2$

2·Phosphoenolpyruvate + E4P ⟶ Aromatic AA + $CO_2$

2·Pyruvate + Acetyl ⟶ Leucine + 2·$CO_2$

Oxaloacetate + Pyruvate ⟶ Isoleucine + $CO_2$

2·Pyruvate ⟶ Valine + $CO_2$

FIG. 11

CONTROLLING METABOLISM BY SUBSTRATE COFEEDING

RELATED APPLICATION

This application claims priority under 35 U.S.C. § 119(e) to U.S. provisional patent application No. 62/527,630, filed Jun. 30, 2017, the entire contents of which are incorporated herein by reference.

GOVERNMENT SUPPORT

This invention was made with Government support under Grant Nos. DE-SC0012377, DE-SC0008744, and DE-AR0000433 awarded by the Department of Energy. The Government has certain rights in the invention.

FIELD

The disclosure provides methods using mixed substrate cofeeding for bioproduct synthesis, which enables faster, more efficient, and higher yield carbon conversion in various organisms.

BACKGROUND

Within each cell, metabolic networks serve as a microscopic chemical plant that can utilize numerous input substrates for cellular needs and bioproduct synthesis (1). However, as our understanding of mixed substrate utilization remains limited, the use of single organic carbon sources has been dominant in both laboratory and industry (2, 3). Despite their simplicity, single substrates naturally impose stoichiometric constraints on available carbons, energy, and redox cofactors, which need to be balanced for optimal product synthesis. Thus, genetic rewiring of metabolic pathways is required to advantageously shift these stoichiometries (4), precluding wide application of non-model organisms that lack suitable genetic tools (5).

Substrate mixtures, on the other hand, present the potential to alleviate such stoichiometric constraints without pathway engineering. Since each substrate has unique efficiencies for carbon, energy, and cofactor generation, varying the relative amounts of substrates in the mixture allows fine-tuning of carbon-to-energy-to-cofactor ratios. Furthermore, substrates with different entry points to metabolism may alleviate protein burdens by providing the required precursors in fewer enzymatic steps. Nevertheless, mixed substrate metabolism is epitomized by sequential (e.g., diauxie) and hierarchical (yet simultaneous) utilization based on substrate preference (6-8), perhaps reflecting the evolutionary fitness of cells in their native environments (9). Recent pioneering work has focused on batch-feeding of substrate mixtures for co-utilization, but these studies require carbon sources that do not trigger catabolite repression, extensive genetic alterations, or prolonged evolutionary engineering (10-14). Thus, the utility of the full mixture spectrum has so far been unexplored and inaccessible.

SUMMARY

Disclosed herein is a simple and universal solution to overcome undesirable substrate preferences, thereby enabling faster, more efficient, and higher yield carbon conversion in various organisms. Absent intervention, organisms will preferentially consume certain carbon sources (also referred to herein as carbon substrates), such as glucose. The substrates that are preferentially consumed by organisms (e.g., glucose), however, may be costly, environmentally detrimental, unavailable, or otherwise undesirable, rendering them undesirable for scientific or commercial purposes. This preferential consumption of such undesirable carbon sources (yet preferred or favored from the point of view of the organism) instead of preferred carbon sources (e.g., carbon dioxide), known as catabolite repression, can be eliminated when the feeding of the organisms' preferred "superior" substrate (e.g., glucose) is controlled to maintain negligible concentrations in the system. This co-feeding approach provides the organisms with a minimal amount of their preferred, yet scientifically or commercially undesirable, carbon substrate, and also supplies ample amounts of a second, more scientifically or commercially desirable carbon source such as carbon dioxide or acetate. Thus, organisms consume the scientifically or commercially desired substrate as the primary carbon source for carbon conversion, and utilize the superior, yet undesirable, substrate only to maintain cell function and complement the production of rate-limiting cofactors with reducing capabilities and high-energy phosphate bond(s). Implementation of this unique co-feeding methodology not only allowed for experimentation within the uncharted metabolic landscape of mixed substrates, but also led to the discovery of synergisms that yielded productivities exceeding the sum of individual substrate-driven productivities.

According to one aspect, methods for converting carbon dioxide into organic compounds are provided. The methods include culturing non-photosynthetic autotrophic cells in a culture vessel containing a fermentation medium comprising: a controlled, limiting amount of carbon substrate, a controlled amount of carbon dioxide ($CO_2$), and a controlled amount of diatomic hydrogen ($H_2$). In some embodiments, the limiting amount of carbon substrate is sufficient to permit the cells to produce adenosine triphosphate (ATP) necessary for cellular maintenance, but insufficient to be incorporated into the organic compounds as a major component.

In some embodiments, the proportion of carbon substrate to $H_2$ is controlled by changing the amount of carbon substrate in the fermentation medium. In some embodiments, the proportion of carbon substrate to $H_2$ is controlled by altering the relative rates at which the substrate and $H_2$ are added into the culture vessel. In some embodiments, the proportion of carbon substrate and/or $H_2$ to the culture volume is controlled by altering the relative rates at which the substrate and/or $H_2$ are added into the culture vessel. In some embodiments, the rate at which the carbon substrate is added to the culture vessel is less than 0.3 grams of carbon substrate per gram of cells (dry weight) per hour.

In some embodiments, the amount of carbon substrate is insufficient to permit the cells to produce sufficient electrons. In some embodiments, the limiting amount of carbon substrate provides less than about 25%, less than about 20%, less than about 15%, less than about 10%, less than about 5%, less than about 2%, or less than about 1% of the quantity of electrons in the culture.

In some embodiments, the amount of $H_2$ is sufficient to provide a quantity of electrons that is equal to or more than the electron deficit resulting from the decreased concentration of carbon substrate. In some embodiments, the quantity of electrons provided by $H_2$ is at least about 75%, at least about 80%, at least about 85%, at least about 90%, at least about 95%, at least about 98%, or at least about 99% of the quantity of electrons in the culture. In some embodiments, the rate of addition of $H_2$ is at least as fast as the maximum gas transfer rate.

In some embodiments, the culture vessel is a semi-batch reactor or continuous reactor. In some embodiments, the continuous reactor is a continuous flow stirred-tank reactor or a continuous bubble column reactor.

In some embodiments, the non-photosynthetic autotrophic cells are acetogenic cells. In some embodiments, the acetogenic cells comprise *Moorella thermoacetica*, *Clostridium ljungdahlii*, or *Acetobacterium woodii*.

In some embodiments, the carbon substrate comprises one or more sugars. In some embodiments, the one or more sugars comprise glucose, fructose, and/or xylose.

In some embodiments, the rate of addition of $CO_2$ is unlimited. In some embodiments, the rate of addition of $CO_2$ is about one half of the rate of addition of $H_2$.

According to another aspect, methods of converting acetyl-CoA into lipids are provided. The methods include culturing oleaginous cells in a culture vessel containing a fermentation medium comprising: a controlled, limiting amount of carbon substrate, and a controlled amount of acetate.

In some embodiments, the oleaginous cells are oleaginous yeast cells. In some embodiments, the oleaginous yeast cells are *Yarrowia lipolytica* cells.

In some embodiments, the carbon substrate is one or more of gluconate, glycerol, and/or a hexose, optionally glucose or fructose.

In some embodiments, the oleaginous cells overexpress a kinase that phosphorylates the carbon substrate. In some embodiments, the carbon substrate is gluconate and the kinase that phosphorylates the carbon substrate is gluconate kinase.

In some embodiments, the amount of the carbon substrate is sufficient to generate reduced nicotinamide adenine dinucleotide phosphate (NADPH) through the oxidative pentose phosphate pathway (oxPPP) and convert acetyl-CoA into lipids, but is insufficient to be incorporated into the lipids as a major component.

In some embodiments, the acetate provides the acetyl-CoA and ATP necessary for converting acetyl-CoA into lipids.

In some embodiments, the proportion of carbon substrate to acetate is controlled by changing the amount of carbon substrate in the fermentation medium. In some embodiments, the proportion of carbon substrate to acetate is controlled by altering the relative rate at which the fermentation medium containing the carbon substrate is added into the culture vessel. In some embodiments, the rate at which the carbon substrate is added to the culture vessel is less than 0.03 grams of carbon substrate per gram of cells (dry weight) per hour. In some embodiments, the initial supplied concentration of acetate is at least 34 grams per liter.

In some embodiments, the culture vessel is a semi-batch or continuous reactor. In some embodiments, the continuous reactor is a continuous flow stirred-tank reactor.

In some embodiments, the amount of acetate in the culture vessel is not depleted during lipid production.

According to another aspect, methods for converting carbon dioxide into lipids are provided. The methods include: (a) culturing non-photosynthetic autotrophic cells according to the methods described herein to produce acetate, and (b) culturing oleaginous cells in a culture vessel containing a fermentation medium comprising: a controlled, limiting amount of carbon substrate, and the acetate produced in (a) to produce lipids.

In some embodiments, the oleaginous cells are oleaginous yeast cells. In some embodiments, the oleaginous yeast cells are *Yarrowia lipolytica* cells.

In some embodiments, the carbon substrate is one or more of gluconate, glycerol, and/or a hexose, optionally glucose or fructose.

In some embodiments, the oleaginous cells overexpress a kinase that phosphorylates the carbon substrate. In some embodiments, the carbon substrate is gluconate and the kinase that phosphorylates the carbon substrate is gluconate kinase.

In some embodiments, the amount of the carbon substrate is sufficient to generate reduced nicotinamide adenine dinucleotide phosphate (NADPH) through the oxidative pentose phosphate pathway (oxPPP) and convert acetyl-CoA into lipids, but is insufficient to be incorporated into the lipids as a major component.

In some embodiments, the acetate provides the acetyl-CoA and ATP necessary for converting acetyl-CoA into lipids.

In some embodiments, the proportion of carbon substrate to acetate is controlled by changing the amount of carbon substrate in the fermentation medium. In some embodiments, the proportion of carbon substrate to acetate is controlled by altering the relative rate at which the fermentation medium containing the carbon substrate is added into the culture vessel. In some embodiments, the rate at which the carbon substrate is added to the culture vessel is less than 0.03 grams of carbon substrate per liter of culture volume per hour. In some embodiments, the initial supplied concentration of acetate is at least 34 grams per liter.

In some embodiments, the culture vessel is a semi-batch or continuous reactor. In some embodiments, the continuous reactor is a continuous flow stirred-tank reactor.

In some embodiments, the amount of acetate in the culture vessel is not depleted during lipid production.

According to another aspect, methods of producing bioproducts are provided. The methods include (a) culturing non-photosynthetic autotrophic cells according to the methods described herein to produce acetate, and (b) culturing cells that utilize acetate to produce bioproducts in a culture vessel containing a fermentation medium comprising: a controlled, limiting amount of carbon substrate, and the acetate produced in (a) to produce the bioproducts. In some embodiments, the bioproducts are oleochemicals, polyketides, or mevalonate pathway derived natural products. In some embodiments, the mevalonate pathway derived natural products are terpenoids or derivatives thereof.

In some embodiments, the carbon substrate is one or more of gluconate, glycerol, and/or a hexose, optionally glucose or fructose.

In some embodiments, the cells of (b) overexpress a kinase that phosphorylates the carbon substrate. In some embodiments, the carbon substrate is gluconate and the kinase that phosphorylates the carbon substrate is gluconate kinase.

In some embodiments, the amount of the carbon substrate is sufficient to generate reduced nicotinamide adenine dinucleotide phosphate (NADPH) through the oxidative pentose phosphate pathway (oxPPP) and convert acetyl-CoA into lipids, but is insufficient to be incorporated into the bioproducts as a major component.

In some embodiments, the acetate provides the acetyl-CoA and ATP necessary for converting acetyl-CoA into bioproducts.

In some embodiments, the proportion of carbon substrate to acetate is controlled by changing the amount of carbon substrate in the fermentation medium. In some embodiments, the proportion of carbon substrate to acetate is controlled by altering the relative rate at which the fermentation medium containing the carbon substrate is added into the culture vessel. In some embodiments, the rate at which the carbon substrate is added to the culture vessel is less than 0.03 grams of carbon substrate per liter of culture volume per hour. In some embodiments, the initial supplied concentration of acetate is at least 34 grams per liter.

In some embodiments, the culture vessel is a semi-batch or continuous reactor. In some embodiments, the continuous reactor is a continuous flow stirred-tank reactor.

In some embodiments, the amount of acetate in the culture vessel is not depleted during lipid production.

According to another aspect, methods are provided that include culturing microbial cells in a culture medium that comprises a plurality of carbon substrates, wherein the mixed carbon substrates comprise at least one carbon substrate that is preferentially utilized by the microbial cells and at least one carbon substrate that is not preferentially utilized by the microbial cells, wherein the at least one carbon substrate that is preferentially utilized by the microbial cells is present in a limiting amount such that the at least one carbon substrate that is not preferentially utilized by the microbial cells provides the majority of the carbon for carbon-based molecules produced by the microbial cells.

In some embodiments, the concentration of the at least one carbon substrate that is preferentially utilized by the microbial cells is maintained in the limiting amount during the culturing of the microbial cells, wherein catabolite repression is not induced.

In some embodiments, the at least one carbon substrate that is preferentially utilized by the microbial cells provides NADPH and/or another cofactor with reducing capabilities to the microbial cells, optionally wherein the cofactor with reducing capabilities is a ferredoxin, NADH, and/or $FADH_2$.

In some embodiments, the at least one carbon substrate that is preferentially utilized by the microbial cells provides ATP and/or another cofactor with high-energy phosphate bond(s) to the microbial cells, optionally wherein the cofactor with high-energy phosphate bond(s) is GTP and/or pyrophosphate.

In some embodiments, the at least one carbon substrate that is preferentially utilized by the microbial cells is present at less than 10%, less than 5%, less than 4%, less than 3%, less than 2%, or less than 1% of the total mixed carbon substrates.

In some embodiments, the at least one carbon substrate that is preferentially utilized by the microbial cells is a part of a multi-substrate mixture. In some embodiments, the multi-substrate mixture is a formulated mixture, optionally a defined culture mixed-substrate media, or a naturally occurring mixture, optionally a hemicellulosic biomass. In some embodiments, the at least one carbon substrate that is preferentially utilized by the microbial cells becomes accessible to the microbial cells by controlled biological, chemical, or thermal decomposition of naturally occurring multi-substrate mixture such as biomass.

In some embodiments, the at least one carbon substrate that is preferentially utilized by the microbial cells is maintained at low or negligible concentrations while being supplied continuously or semi-continuously to a reactor in which the microbial cells are cultured.

BRIEF DESCRIPTION OF THE DRAWINGS

(FIG. 1A) Acetate can efficiently support acetyl-CoA and adenosine triphosphate (ATP) generation through the TCA cycle but not NADPH generation, which requires many enzymatic steps and ATP. Glucose, on the other hand, can produce NADPH more directly through oxPPP. (FIG. 1B) Since glucose batch feeding suppresses acetate consumption, glucose was continuously supplemented in small quantities to the acetate culture. (FIG. 1C) Despite the continuous feeding of glucose, its concentration in the reactor remained at 0 and acetate concentration decreased. Thus, the fed-batch system enabled simultaneous consumption of acetate and glucose. (FIG. 1D) Biomass and (FIG. 1E) lipid production was faster and higher with glucose-"doping" compared to the acetate-only control.

(FIG. 2A) Glucose, fructose, glycerol, and gluconate enter central carbon metabolism through upper glycolysis and PPP. (FIG. 2B) Supplementation of these four substrates accounted for ~5% of the total carbon consumed by the cells and the primary carbon source was acetate. (FIG. 2C) Specific growth rates nearly doubled with substrate cofeeding compared to the acetate-only control. (FIG. 2D) Growth phase (nitrogen-replete) specific lipid productivity nearly doubled with substrate cofeeding. (FIG. 2E) Lipogenic phase (nitrogen-depleted) specific lipid productivity was mildly enhanced by glucose, fructose, or glycerol supplementation. Gluconate-"doping" significantly outperformed the other conditions.

(FIG. 3A) Tracing carbons from $[U-^{13}C_6]$ gluconate revealed partitioned usage of metabolism. The heavy $^{13}C$ of gluconate remained mainly in upper glycolysis and PPP. Acetyl-CoA and TCA intermediates were completely unlabeled, indicating exclusive contribution from acetate. (FIG. 3B) Metabolic flux analysis via isotope mass balancing revealed the cyclic reaction sequence generating NADPH. The "pentose cycle" consisted of the NADPH-producing oxPPP, transketolase, transaldolase, and phosphoglucose isomerase. Flux values are in mmol $gCDW^{-1}$ $hr^{-1}$.

(FIG. 4A) The reductive acetyl-CoA pathway consists of the carbonyl and methyl branches for conversion of carbon dioxide ($CO_2$) into acetyl group. The methyl branch requires ATP. (FIG. 4B) Analysis of carbon input and output in batch cofeeding of *M. thermoacetica* with glucose and $CO_2$ revealed the preferential use of glucose. (FIG. 4C) Batch cofeeding $[U-^{13}C_6]$glucose and $CO_2$ revealed the simultaneous use of glucose and $CO_2$. Glucose carbons contributed mainly to glycolysis and PPP while partially to TCA cycle. A substantial fraction of TCA carbos was traced to $CO_2$. (FIG. 4D) Despite simultaneous utilization of $CO_2$, preferred glucose use led to excessive decarboxylation. Flux values are in mmol $gCDW^{-1}$ $h^{-1}$ of acetyl-CoA.

(FIG. 5A) Since glucose batch feeding leads to excessive decarboxylation, glucose was continuously supplemented in small quantities to gas-fermenting *M. thermoacetica* culture. (FIG. 5B, FIG. 5C) Acetate productivity, yield, and $CO_2$ fixation rate at varying ratios of electrons (e) derived from $H_2$ and glucose. (FIG. 5B) Acetate productivity peaked when ~90% of $e^-$ were derived from $H_2$ and ~10% glucose. On the other hand, carbon yield (acetate produced per glucose consumed) increased with increasing fraction of electrons from H$_2$. (FIG. 5C) CO$_2$ fixation rate peaked when ~10% of e$^-$ were derived from glucose and remained high near the autotrophic limit.

(FIG. 6A) Glucose- and gluconate-"doping" resulted in synergy that accelerated acetogenesis and lipogenesis beyond the linear extrapolation of additional carbon supplement. (FIG. 6B) The maximum CO$_2$ fixation and fatty acid production rates were attained by cofeeding glucose and gluconate in minor quantities. Stoichiometric analysis of metabolic requirements and burdens revealed the key role of glucose and gluconate in generating ATP and NADPH. The dashed arrows denote negligible contributions. (FIG. 6C) In terms of energy efficiency, 95% of H$_2$ energy can be stored as acetate by M. thermoacetica and 55% of acetate energy can be stored as lipids by Y. lipolytica. Coordination of acetogenesis and lipogenesis enabled storage of 38% of H$_2$ energy as lipids and 14% as biomass.

(FIG. 9A) Lipid concentration over time in glucose, fructose, glycerol, and gluconate supplemented cultures compared to the acetate-only control condition. (FIG. 9B) Cell dry weight over time in glucose, fructose, glycerol, and gluconate supplemented cultures compared to the acetate-only control condition.

(FIG. 10A, FIG. 10B) Tracing $^{13}$C from [U-$^{13}$C$_6$] glucose in M. thermoacetica. (FIG. 10A) Cellular CO$_2$ labeling was inferred by comparing the labeling of citrulline and ornithine. (FIG. 10B) Headspace CO$_2$ labeling as measured by GC-MS was consistent with the cellular CO$_2$ labeling.

FIG. 11. Necessary CO$_2$ producing pathways. Examples of biomass precursor synthesis pathways necessary for cell growth that produce CO$_2$.

DETAILED DESCRIPTION

Figure 1:
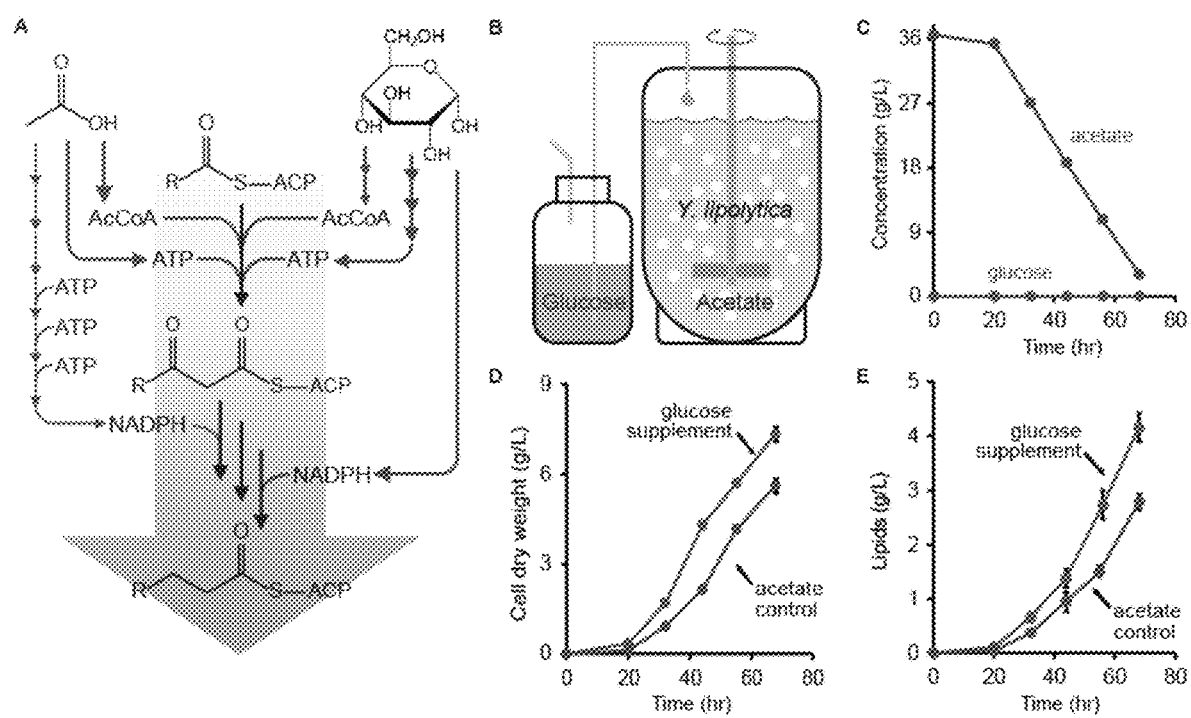
FIGS. 1A-1E. Continuous glucose cofeeding relieves repression of acetate in *Y. lipolytica*.

One of the greatest biotechnological challenges is engineering metabolism. Metabolic engineering efforts have typically focused on funneling metabolic fluxes through product synthesis pathways via assembling various gene pools that exist in nature and knocking out competing pathways(29). Such approaches set a limit on the choice of microbial hosts based on genetic manipulability. In addition, most processes start from glucose as the sole substrate. Sugars are an abundant feedstock, but there remain issues of renewably and cost-effectively supplying these substrates in large volumes without deterring food supply(30). More broadly, using a single substrate in fermentations inherently causes some metabolic intermediates to be out of balance and surplus components to be wasted because of the differences in chemical properties between the substrate and the product. Although recent efforts have begun to address this issue(4), the strategies employ extensive network analysis and engineering solutions that may not be widely generalizable to all organisms.

Here the potential of mixed substrate cofeeding as a more effective starting point for bioproduct synthesis was demonstrated. As the first step, the difficulties that arise due to organisms' preferential substrate usage were overcome. Controlled continuous feeding of a preferred substrate did not inhibit the consumption of the less favored substrate. Using this approach, the goal was to enhance the utilization of CO$_2$ and acetate, which are typically the end products of metabolism and therefore least preferred by organisms. This was demonstrated with the cofeeding of glucose and gases (CO$_2$ and H$_2$) to M. thermoacetica as well as gluconate and acetate to Y. lipolytica. Correspondingly, this design should be widely applicable to various substrates and organisms.

Unexpectedly, substrate cofeeding synergistically enhanced product synthesis. In both cases, the total product carbon flux resulting from co-utilized substrates ($V_{12}$) exceeded the sum of the individual fluxes ($V_1+V_2$). However, previous models describing substrate co-utilization have overlooked this synergistic effect(11). The observation of $V_{12}>V_1+V_2$ could be explained by the two substrates having distinct yet complementary functions in cellular metabolism. Stoichiometric analysis of metabolic requirements and burdens suggested that glucose and gluconate could indeed complement ATP and NADPH generation, alleviating the limitations seen in acetogenesis and lipogenesis, respectively. By substrate cofeeding, metabolism was rewired without genetic engineering to balance the stoichiometric ratios of these metabolic intermediates and to better satisfy cells' metabolic needs for accelerated product synthesis.

Cofeeding $^{13}$C-labeled glucose and gluconate revealed that nearly all of these supplements went into ATP and NADPH production, respectively. Furthermore, pyruvate kinase (PEP+ADP→Pyr+ATP) in M. thermoacetica and the pentose cycle (6PG→R5P→F6P→G6P→6PG+2 NADPH) in Y. lipolytica were identified as important cofactor generating steps. Activating pyruvate kinase by glucose cofeeding solved the challenge of slow CO$_2$ fixation, which is due to ATP-limited metabolism in autotrophic fermentations(28, 31). Activating the pentose cycle by gluconate cofeeding solved the challenge of limited NADPH production through oxPPP in acetate-fed cells. Importantly, the observed significant enhancements in CO$_2$ and acetate metabolism required only minor addition of "valuable" glucose and gluconate.

The substrate doping scheme can be valuable in a variety of biotechnological applications. The demonstration of CO$_2$/H$_2$-to-acetate-to-lipids conversion at high productivity and energetic efficiency serves as an important example of renewable energy storage using substrates that do not interfere with food supply. Since acetate is closely related to acetyl-CoA, a focal point in many metabolic pathways, other acetate-based processes with metabolic dopants could enable rapid synthesis of a wide repertoire of bioproducts such as fatty acid derived oleochemicals(32) and mevalonate pathway derived natural products(33). By coupling this to the glucose-doped acetogenesis, $CO_2$ could become the initial feedstock for all subsequent acetate-driven processes, benefiting both the environment and carbon economy. Moreover, the metabolic enhancements by cofeeding superior substrates is not limited to $CO_2$- and acetate-based fermentations. The imbalance of carbon building blocks, cofactors, and energy with respect to the desired product requirement can also be seen in many other single-substrate substrate bioconversions. In these cases, identification of complementary substrates would improve the coordination of pathway usage in complex biosynthesis networks and provide increased quantities of the limiting element. Consequently, substrates previously considered infeasible for industrial bioprocesses due to limited productivity may become well-suited as economically and technologically viable feedstocks(34).

The substrate cofeeding scheme was applied to two widely divergent organisms to optimize reductive metabolism of lipogenesis and acetogenesis. The oleaginous yeast *Y. lipolytica* was cultured on acetate and continuously fed limiting quantities of glucose, fructose, glycerol, or gluconate. In this fed-batch setup, cells simultaneously consumed acetate and the supplemented substrate. While acetate remained the primary carbon source, "doping" the culture with the superior substrates doubled lipogenic rates compared to the acetate-only control. It was identified that gluconate doping performed best in this regard. Tracing $^{13}C$ from gluconate revealed that obligatory NADPH synthesis by recursive use of the oxidative pentose phosphate pathway (oxPPP) was responsible for the observed synergy with acetate.

With the ultimate goal of sourcing lipid carbons from $CO_2$, $CO_2$-fixing acetogenesis was first optimized. It was initially observed that the acetogenic bacterium *M. thermoacetica* simultaneously consumes $CO_2$ and glucose with the latter providing ATP and electrons ($e^-$) necessary for $CO_2$ fixation, cell maintenance, and growth. However, tracing $^{13}C$-labeled glucose revealed that glucose metabolism dominated and $e^-$ generation was coupled to excessive decarboxylation. To shift cellular metabolism towards greater $CO_2$ incorporation, a chemostat that continuously supplied limiting glucose and ample $H_2$ was designed. Under these conditions, $CO_2$ metabolism dominated, glucose primarily produced ATP only sufficient for cell maintenance via pyruvate kinase, and carbon-free $e^-$ for net $CO_2$ reduction was supplied by $H_2$. Importantly, with glucose doping, *M. thermoacetica* rapidly converted $CO_2$ into acetate exclusively, which we used for lipid production in gluconate-doped *Y. lipolytica*.

With the synergy between mixed substrates, $CO_2$ was converted at 2.2 g per g cell dry weight per hour (g $gCDW^{-1}$ $hr^{-1}$), substantially faster than ~0.05 g $gCDW^{-1}$ $hr^{-1}$ of typical photosynthetic systems(15). Similarly, lipids were produced at 0.046 g $gCDW^{-1}$ $hr^{-1}$ from acetate, faster than ~0.02 g $gCDW^{-1}$ $hr^{-1}$ of a previously optimized system(16). Coordinating the glucose-doped acetogenic and gluconate-doped lipogenic processes, carbons in the most oxidized and undesirable state ($CO_2$) were converted to the most energy-dense state (lipids) while storing 38% of energy from $H_2$. By controlling metabolic pathways on a systems level via substrate cofeeding, the limitation of ATP and NADPH dependency in biological catalysis was overcome.

Provided herein are methods for converting carbon dioxide into organic compounds (e.g., carbon fixation). Many of the non-photosynthetic carbon fixation pathways belong to anaerobic metabolism. These pathways have been hypothesized to be similar to the primordial activity of life billions of years ago, where inorganic compounds were plentiful and organism complexity was very low. Three of them are the (1) reductive acetyl CoA pathway (also referred to as the Wood-Ljungdahl pathway herein), (2) reductive TCA Cycle, and (3) 3-hydroxypropionate pathway (Raymond 2005. Reviews Mineralogy Geochemistry 59: 211-31), of which the most prominent is the Wood-Ljungdahl pathway. While other pathways for carbon fixation are cyclic, requiring the recycling of intermediates, the Wood-Ljungdahl pathway is the only linear pathway known to fix carbon.

Besides using the Wood-Ljungdahl pathway to grow by using $CO_2$ as a sole carbon source, some bacteria (e.g., acetogens) employ this pathway in order to maximize yield when grown with other substrates (e.g., glucose). Acetogens do this, for example, by consuming glucose normally by glycolysis, which produces $CO_2$, reducing equivalents (e.g., NADH), and carbon for biomass or product (e.g., pyruvate). In certain circumstances, the cell can recover the $CO_2$ by using those same reducing equivalents to form acetyl-CoA (Muller 2003. Appl Environ Microbiol. 69: 6345-53). This allows acetogens to exhibit a maximum theoretical yield of 100%. All glucose consumed is metabolized to acetate, rather than the 50-60% as observed in many other organisms (U.S. Pat. No. 6,509,180).

The term "acetogen" or "acetogenic microbe" or "acetogenic bacterium" is art-recognized and refers to a microorganism (also referred to as a microbe or microbial cell herein) that generates acetate (also referred to interchangeably herein as acetic acid) as a product of anaerobic $CO_2$ fixation (as used herein, $CO_2$ includes gaseous and dissolved carbon dioxide, as well as the ionic forms of carbon dioxide, such as carbonate and bicarbonate). Acetogens are found in a variety of anaerobic habitats and can use a variety of compounds as sources of energy and carbon; the best studied form of acetogenic metabolism involves the use of carbon dioxide as a carbon source and hydrogen as an energy source.

The methods provided herein include culturing non-photosynthetic autotrophic cells, such as acetogens, in a culture vessel containing a fermentation medium comprising: a controlled, limiting amount of carbon substrate (which is not $CO_2$), a controlled amount of $CO_2$, and a controlled amount of $H_2$. By culturing the non-photosynthetic autotrophic cells in this manner, $CO_2$ can be fixed from, e.g., atmospheric sources. The carbon from the $CO_2$ provides most if not all of the carbon needed to produce acetate or other organic compounds of the cells. However, because $CO_2$ does not produce ATP, a limiting amount of a carbon substrate is added to the culture to provide ATP production, e.g., for cellular maintenance. The limiting amount of a carbon substrate may also provide some electrons to the culture, but because it is present in a limiting amount, it does not provide sufficient electrons for production of acetate (or other organic compounds). To supplement the limited amount of electrons, a source of electrons such as $H_2$ is provided to the culture. As shown herein, when even a limiting amount of carbon substrate is included, fixation of carbon from $CO_2$ is surprisingly and substantially enhanced.

The term "carbon substrate" is known in the art, and refers to a carbon-based component that is contained in the culture medium, and that supplies the cultured organism with carbon and energy to perform varied cellular functions. In some embodiments, the carbon substrate is any sugar substrate that is consumed by the cell. For example, in some embodiments, the carbon substrate is any one of the following sugars: glucose, fructose, galactose, xylose, gluconate, glycerol, or other hexose sugars (e.g., allose, altrose, gulose, idose, talose, psicose, tagatose, and sorbose).

Figure 13:
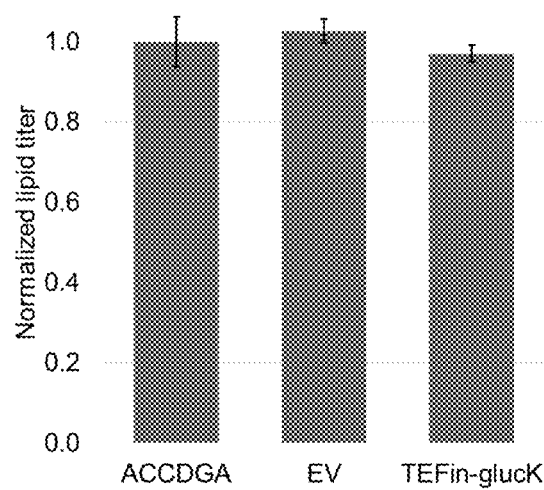
FIG. 13. Overexpression of gluconate kinase does not affect lipid production. Normalized lipid titers after 72 hr of culture in acetate media. ACCDGA is the original unmodified Y. lipolytica strain. EV is a strain carrying an empty control vector stably integrated into the genome while TEFin-glucK is a strain overexpressing Y. lipolytica native gluconate kinase under the TEFin promoter through genome integration.

The cellular consumption of a carbon substrate such as glucose, gluconate, or other related sugars described herein may be rate-limited by the availability of an enzyme that catalyzes the transfer of a phosphate group from ATP to a specified molecule (e.g., a kinase). To minimize the potential of limited kinase availability acting as a rate-limiting step in the cellular consumption of carbon, some embodiments include the overexpression of a kinase that is associated with the provided carbon substrate such as glucose, gluconate, or other related sugars described herein. This is to ensure that uptake of the carbon substrate, such as glucose, gluconate, or other related sugars described herein, and incorporation into central carbon metabolism is not inhibited by inadequate levels of the kinase. For example, in some embodiments the oleaginous cells overexpress gluconate kinase (FIG. 13). Overexpression of a kinase in some embodiments is performed under control of a TEFin promoter that is operably linked to a nucleic acid sequence encoding the kinase. In some embodiments, overexpression of a kinase under a TEFin promoter is performed through genome integration.

While other carbon substrates, such as $CO_2$, may provide the carbon necessary for the cell to perform varied cellular functions, including the carbon needed to produce acetate or other organic compounds of the cells, cells do not utilize all carbon substrates equivalently. For example, in some embodiments multiple carbon substrates, such as $CO_2$, and a second carbon substrate (e.g., glucose) are provided to the cultured cells in a substrate mixture. In a substrate mixture such as this, mixed substrate metabolism is epitomized by sequential (e.g., diauxie) and hierarchical (yet simultaneous) utilization based on substrate preference (see references 6-8 listed below), In an exemplary embodiment, where glucose and $CO_2$ comprise the carbon substrates in the substrate mixture, cultured cells may preferentially consume glucose. This concept is known as "catabolite repression." In some embodiments, a carbon substrate such as glucose, gluconate, or other sugars described herein is a "carbon substrate that is preferentially utilized by microbial cells." Conversely, in some embodiments $CO_2$ is a "carbon substrate that is not preferentially utilized by microbial cells." The methods provided herein overcome catabolite repression by limiting the amount of carbon substrate that is preferentially utilized by microbial cells, such as glucose, gluconate, or other sugars described herein, that is provided to the cell culture.

In some embodiments, the limiting amount of carbon substrate is sufficient to permit the cells to produce ATP necessary for cellular maintenance, but insufficient to be incorporated into the organic compounds as a major component of the organic compounds. For example, by "insufficient to be incorporated into the organic compounds as a major component of the organic compounds" is meant that the carbon from the limiting amount of carbon substrate provides less than 50%, 45%, 40%, 35%, 30%, 25%, 20%, 15%, 10%, 5%, 4%, 3%, 2%, or 1% (or even essentially 0%) of the carbon in acetate or other organic compounds produced by the cells. In contrast, $CO_2$ provides the majority of the carbon for acetate or other organic compounds produced by the microbial cells, such as more than 50%, 55%, 60%, 65%, 70%, 75%, 80%, 85%, 90%, 95%, 96%, 97%, 98%, 99%, (or even essentially 100%) of the carbon for acetate or other organic compounds produced by the microbial cells.

In some embodiments, the proportion of carbon substrate to $H_2$ is controlled by changing the amount of carbon substrate in the fermentation medium and/or by altering the relative rates at which the carbon substrate and $H_2$ are added into the culture vessel. For example, in some embodiments, the rate at which the carbon substrate is added to the culture vessel is less than 0.3 grams of carbon substrate per gram of cells (dry weight) per hour, such as less than 0.2, less than 0.1, less than 0.05, less than 0.025, less than 0.0025, or less than 0.0005 grams of carbon substrate per gram of cells (dry weight) per hour. In other embodiments, the rate at which the carbon substrate is added to the culture vessel is higher than 0.3 but less than 0.6 grams of carbon substrate per gram of cells (dry weight) per hour, such as less than 0.5, or less than 0.4 grams of carbon substrate per gram of cells (dry weight) per hour.

In some embodiments, the restriction of carbon substrate results in an amount of carbon substrate that is insufficient to permit the cells to produce sufficient electrons for production of acetate (or other organic compounds). For example, in some embodiments, this limiting amount of carbon substrate provides less than about 25%, less than about 20%, less than about 15%, less than about 10%, less than about 5%, less than about 2%, or less than about 1% of the quantity of electrons in the culture.

To supplement the insufficient amount of electrons, an unlimited amount of $H_2$ is provided to the cell culture. In some embodiments, the amount of $H_2$ is sufficient to provide a quantity of electrons that is equal to or more than the electron deficit resulting from the decreased concentration of carbon substrate. For example, in some embodiments, the quantity of electrons provided by $H_2$ is at least about 75%, at least about 80%, at least about 85%, at least about 90%, at least about 95%, at least about 98%, or at least about 99% of the quantity of electrons in the culture.

A culture vessel may be alternately referred to as a fermentor, and may contain either aerobic or anaerobic conditions and a fermentation medium to suit the needed environments of the organisms in culture. The term "fermentor" or "culture vessel" refers to an enclosure, or partial enclosure, in which a biological and/or chemical reaction takes place, at least part of which involves a living organism or part of a living organism. Where liquid cultures are used for fermentation, the fermentor is typically a culture vessel able to hold the desired amount of liquid media. If a gaseous phase is employed in the fermentation process, the fermentor employed will have a volume allowing accommodation of the gaseous phase and, if the gaseous phase is not air, the fermentor is typically sealed in an airtight manner Typically, a fermentor comprises one or more inflows and/or outflows for the introduction and/or removal of liquids, solids, and/or gas into and/or out of the fermentor.

Suitable fermentor configurations will be apparent to those of skill in the art. For example, in some embodiments, a continuous stirred tank reactor (CSTR), a bubble column reactor (BCR), a semi-batch reactor, or a trickle bed reactor (TBR), may be employed. In some embodiments, a fermentor comprises a culture of microbial cells performing the fermentation process. In some embodiments, a fermentor may continuously or semi-continuously be fed with new microbes from a growth or culture vessel.

Depending on the fermentation scale, fermentors can range from volumes of milliliters to thousands of liters or more. Some fermentors may include cell cultures where microbes (also referred to as microbial cells herein) are in contact with moving liquids and/or gas bubbles. Microbes or microbe cultures may be grown in suspension or attached to solid phase carriers. Non-limiting examples of carrier systems include microcarriers (e.g., polymer spheres, microbeads, and microdisks that can be porous or non-porous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multicartridge reactors, and semi-permeable membranes that can comprising porous fibers), microcarriers having reduced ion exchange capacity, encapsulation cells, capillaries, and aggregates. Carriers can be fabricated from materials such as dextran, gelatin, glass, and cellulose.

The term "aerobic conditions" is art recognized and refers to conditions that provide sufficient oxygen for efficient oxidation of a carbon source by an aerobic organism. In some embodiments, aerobic conditions are conditions that provide an abundance or even an overabundance of oxygen, for example, in the form of micro-bubbles of oxygen in a liquid medium. For example, a fermentor comprising a gaseous phase comprising at least 10%, at least 15%, at least 20%, at least 30%, at least 50%, or more oxygen is referred to as an aerobic fermentor.

In some embodiments, an organism performing acetate-driven lipogenesis (e.g., oleaginous cells) is cultured in an aerobic fermentor in a suitable liquid medium. In some embodiments, the liquid medium comprises vitamins and minerals sufficient to permit growth of the microorganism used. Suitable liquid media for aerobic microbe culture are known to those of skill in the art.

The term "anaerobic conditions" is art recognized and refers to conditions that do not provide sufficient oxygen for efficient carbon oxidation by an aerobic organism. In some embodiments, anaerobic conditions are characterized by the essential absence of oxygen. In other embodiments, the oxygen content is less than required by a microbe employed to efficiently oxidize a carbon source. For example, a fermentor comprising a liquid medium and a gaseous phase comprising less than 5%, less than 2%, less than 1%, less than 0.5%, less than 0.1%, less than 0.01%, or less than 0.001% oxygen is referred to as an anaerobic fermentor.

In some embodiments, the $CO_2$ fixing bacteria (e.g., the acetogen) is cultured in the anaerobic fermentor in a suitable liquid medium. In some embodiments, the liquid medium comprises vitamins and minerals sufficient to permit growth of the microorganism used. Suitable liquid media for anaerobic microbe culture are known to those of skill in the art. In some embodiments, the suitable liquid medium includes an unlimited amount of $CO_2$ and/or an unlimited rate of addition of $CO_2$. In some embodiments, the rate of addition of $CO_2$ is about one half of the rate of addition of $H_2$, the latter of which is added to provide electrons as described elsewhere herein.

The term "culturing" refers to maintaining a culture of an organism, for example, a microbe described herein, for a period of time, generally, for a period of time sufficient for a desired fermentation process to be carried out by the microbe. In some embodiments, the culture comprises a microbe described herein and a medium, for example, a liquid medium.

In some embodiments, the culture comprises a carbon source, for example a carbon source dissolved in the culture medium. For example, in some embodiments, a microbe is cultured in an aerobic fermentor in a liquid medium in the presence of a carbon source (e.g., acetate, or a soluble sugar) dissolved in the medium. In some embodiments, the culture comprises a salt and/or buffer establishing conditions of salinity, osmolarity, and pH, that are amenable to survival, growth, and/or conversion of the carbon source to a biofuel or biofuel precursor by the cultured organism.

In some embodiments, the culture comprises one or more additional components, for example, an additive. Non-limiting examples of additives are nutrients, enzymes, amino acids, albumin, growth factors, enzyme inhibitors (for example protease inhibitors), fatty acids, lipids, hormones (e.g., dexamethasone and gibberellic acid), trace elements, inorganic compounds (e.g., reducing agents, such as manganese), redox-regulators (e.g., antioxidants), stabilizing agents (e.g., dimethylsulfoxide), polyethylene glycol, polyvinylpyrrolidone (PVP), gelatin, antibiotics (e.g., Brefeldin A), salts (e.g., NaCl), chelating agents (e.g., EDTA, EGTA), and enzymes (e.g., cellulase, dispase, hyaluronidase, or DNase). In some embodiments, the culture may comprise a compound, for example, a small molecule compound or drug, inducing or inhibiting transcription from a conditional or inducible promoter, for example doxicycline, tetracycline, tamoxifen, IPTG, hormones, or metal ions.

While the specific culture conditions, for example, the concentration of the carbon source, will depend upon the respective microorganism to be cultured, general methods and culture conditions for the generation of microbial cultures are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology*, Part A, Volume 194 (Methods in Enzymology Series, 194), Academic Press (Mar. 11, 2004); Christine Guthrie and Gerald R. Fink, *Guide to Yeast Genetics and Molecular and Cell Biology*, Part B, Volume 350 (Methods in Enzymology, Vol 350), Academic Press; 1st edition (Jul. 2, 2002); and Christine Guthrie and Gerald R. Fink, *Guide to Yeast Genetics and Molecular and Cell Biology*, Part C, Volume 351, Academic Press; 1st edition (Jul. 9, 2002), all of which are incorporated by reference herein.

The Wood-Ljungdahl pathway, described above, exists in several organisms, best known among them being the acetogenic *Clostridia*, such as *Clostridium aceticum, Clostridium difficile, Moorella thermoacetica* (formerly *Clostridium*) and *Acetobacterium woodii*. Besides a strong medical interest in these organisms, it is also noted that *Clostridia* have been the organism of choice for the biological production of solvents and butanol.

Suitable organisms and culture/fermentation conditions for conversion of $CO_2$ to a carbon-based molecule that can be used as a carbon substrate by other microbial cells, for example, acetate (which may also be referred to as acetic acid herein), butanol, or ethanol are described herein and additional suitable organisms and culture/fermentation conditions are well known to those of skill in the art and include, but are not limited to the organisms and culture or fermentation conditions described in International Patent Application Publication Nos: WO2009/105372; WO2007/117157; WO2008/115080; and WO2009/064200; the entire contents of each of which are incorporated herein by reference.

Additional suitable organisms and culture/fermentation conditions include, but are not limited to, those described in Das, A. and L. G. Ljungdahl, *Electron Transport System in Acetogens*; Drake, H. L. and K. Kusel, *Diverse Physiologic Potential of Acetogens*; Chapters 14 and 13 of *Biochemistry and Physiology of Anaerobic Bacteria*, L. G. Ljungdahl eds,. Springer (2003); U.S. Patent Application Publication No. 2007/0275447 entitled "Indirect Or Direct Fermentation of Biomass to Fuel Alcohol," (e.g., *Clostridium carboxidivorans*); and U.S. Pat. No. 7,704,723 entitled "Isolation and Characterization of Novel Clostridial Species," (e.g., *Clostridium ragsdalei*); the entire contents of each of which are incorporated herein by reference.

Additional suitable microorganisms include, but are not limited to, *Butyribacterium methylotrophicum* (see, e.g., "*Evidence for Production of n-Butanol from Carbon Monoxide by Butyribacterium methylotrophicum*," Journal of Fermentation and Bioengineering, vol. 72, 1991, p. 58-60; "*Production of butanol and ethanol from synthesis gas via fermentation*," FUEL, vol. 70, May 1991, p. 615-619); *Clostridium ljungdahli*, (see, e.g., U.S. Pat. Nos. 6,136,577; 5,173,429, 5,593,886, and 6,368,819; International Patent Application Publication Nos WO 00/68407; WO 98/00558 and WO 02/08438; and European Patent EP 117309); *Clostridium autoethanogenum* (see, e.g., Aribini et al, Archives of Microbiology 161: pp 345-351); *Moorella* sp. (see, e.g., Sakai et al, Biotechnology Letters 29: pp 1607-1612). The entire contents of each of the above listed publications is incorporated herein by reference.

In some embodiments, the $CO_2$ fixing bacteria are non-photosynthetic autotrophic cells. Non-photosynthetic autotrophic cells may, in some embodiments, be acetogenic cells. In some embodiments, the acetogenic bacterium is a *Clostridium, Moorella, Oxobacter, Peptostreptococcus, Acetobacterium, Eubacterium, Desulfotomaculum, Archaeglobulus* or *Butyribacterium*, for example, *Clostridium carboxidivorans, Butyribacterium methylotrophicum, Clostridium tetanomorphum, Clostridium autoethanogenum, Clostridium ljungdahlii, Clostridium carboxidivorans, Clostridium tetanomorphum, Oxobacter pfennigii, Peptostreptococcus productus, Acetobacterium woodii, Eubacterium limosum, Butyribacterium methylotrophicum, Moorella thermoacetica, Moorella thermoautotrophica, Desulfotomaculum kuznetsovii, Desulfotomaculum thermobenzoicum*, or *Archaeoglobulus fulgidis*.

Additional acetogens suitable for use in the methods and anaerobic fermentors disclosed herein will be apparent to those of skill in the art. It will also be appreciated that, while in preferred embodiments a homogeneous culture of acetogens of a single strain is employed, a mixed culture of two or more acetogens may also be used in a $CO_2$ fixation process or fermentor as provided herein.

Also described herein are methods to convert acetyl-CoA (i.e., acetyl coenzyme A) into lipids. The term "lipid" is known in the art and refers to fatty acids and their derivatives. Accordingly, examples of lipids include fatty acids (FA, both saturated and unsaturated); glycerides or glycerolipids, also referred to as acylglycerols (such as monoglycerides (monoacylglycerols), diglycerides (diacylglycerols), triglycerides (triacylglycerols, TAGs, or neutral fats); phosphoglycerides (glycerophospholipids); nonglycerides (sphingolipids, sterol lipids, including cholesterol and steroid hormones, prenol lipids including terpenoids, fatty alcohols, waxes, and polyketides); and complex lipid derivatives (sugar-linked lipids or glycolipids, and protein-linked lipids). Lipids are an essential part of the plasma membrane of living cells and microbes. Some cells and microbes also produce lipids to store energy, for example in the form of triacylglycerols in lipid droplets. The term "acetyl-CoA" is known in the art and refers to a molecule that participates in lipid metabolism, among other processes, and delivers the acetyl group necessary to various cellular functions.

The conversion of acetyl-CoA into lipids (or other fatty acids) is a cellular process known as "lipogenesis." Lipogenesis is a term known in the art, and requires both acetyl-CoA and a carbon substrate as described herein. In some embodiments, lipogenesis is achieved by culturing oleaginous cells in a culture vessel containing a fermentation medium comprising: a controlled, limiting amount of carbon substrate (which is not acetate), and a controlled amount of acetate. In some embodiments, the culture vessel is a continuous flow stirred-tank reactor. In other embodiments, the culture vessel is a semi-batch reactor. Continuous flow stirred-tank reactors and semi-batch reactors are known in the art, and are described elsewhere herein.

By culturing the oleaginous cells in this manner, energy can be stored in the form of lipids using acetate as the main source of acetyl-CoA and ATP. However, because acetate does not efficiently produce the reduced nicotinamide adenine dinucleotide phosphate necessary to convert acetyl-CoA into lipids, a limiting amount of carbon substrate is added to the culture volume to produce NADPH and/or another cofactor with reducing capabilities to the microbial cells, such as a ferredoxin, NADH, or $FADH_2$. The carbon substrate is limited to avoid catabolite repression, which results in the preferential consumption by the cells of acetate. As described herein, acetate can be efficiently and reliably produced through the fixation of $CO_2$, which is an abundant carbon feedstock that does not interfere with food supply, and thus consumption of acetate in the production of lipids is both an environmentally and economically ideal method of energy storage.

In some embodiments, the oleaginous cells are oleaginous yeast cells that utilize acetate for cell growth and product synthesis. For example, in some embodiments the oleaginous yeast cells are *Yarrowia lipolytica* cells. *Y. lipolytica* is a non-pathogenic oleaginous yeast that can use a variety of carbon sources, including organic acids, hydrocarbons and various fats and oils. The term "oleaginous" refers to a microbe that can accumulate more than 20% of its dry cell weight as lipid (see C. Ratledge et al., *Microbial routes to lipids*. Biochem Soc Trans. 1989 December; 17(6):1139-41). Exemplary oleaginous cells include yeasts such as *Yarrowia lipolytica, Candida 107, Rhodotorula glutinis, Rhodosporidium toruloides, Cryptococcus curvatus, Trichosporon pullulan, Lipomyces lipofer, Schwanniomyces occidentalis* and other species from among *Yarrowia, Lipomyces, Rhodosporidium* and *Cryptococcus*; oleaginous bacteria such as those *Rhodococcus, Acinetobacter* and *Streptomyces*; and oleaginous algae and microalgae.

Because acetate does not efficiently produce the reduced NADPH necessary to convert acetyl-CoA into lipids, in some embodiments a limiting amount of carbon substrate (which is not acetate) is added to the culture volume. Carbon substrates are described elsewhere herein. In some embodiments, the amount of the provided carbon substrate is sufficient to generate NADPH through the oxidative pentose phosphate pathway (oxPPP) and convert acetyl-CoA into lipids, but is insufficient to be incorporated into the lipids as a major component. The oxPPP pathway is known in the art, and is a metabolic pathway that generates NADPH, pentoses, and ribose 5-phosphate. NADPH is generated in the oxidative phase of the oxPPP pathway. For example, by "insufficient to be incorporated into the lipids as a major component" is meant that the carbon from the limiting amount of carbon substrate provides less than 50%, 45%, 40%, 35%, 30%, 25%, 20%, 15%, 10%, 5%, 4%, 3%, 2%, or 1% (or even essentially 0%) of the carbon in lipids or other organic compounds produced by the cells. By contrast, acetate provides the majority of the carbon for lipids or other organic compounds produced by the microbial cells, such as more than 50%, 55%, 60%, 65%, 70%, 75%, 80%, 85%, 90%, 95%, 96%, 97%, 98%. 99%, (or even essentially 100%) of the carbon for lipids or other organic compounds produced by the microbial cells.

Avoiding catabolite repression in cultured microbial cells, by providing limiting amounts of carbon substrates that are preferentially utilized by the microbial cells (such as glucose, gluconate, or other sugars described herein), results in the microbial cells utilizing acetate as the primary source of the acetyl-CoA used by the microbial cells for lipid production. In some embodiments, therefore, the acetate provides the acetyl-CoA and ATP necessary for converting acetyl-CoA into lipids. In some embodiments, acetate provides the majority of the acetyl-CoA and ATP necessary for the production of lipids or other fatty acids produced by the microbial cells, such as more than 50%, 55%, 60%, 65%, 70%, 75%, 80%, 85%, 90%, 95%, 96%, 97%, 98%. 99%, (or even essentially 100%) of the acetyl-CoA and ATP for lipids or other fatty acids produced by the microbial cells.

In some embodiments, the proportion of carbon substrate relative to acetate is controlled by changing the amount of carbon substrate in the fermentation medium and/or by altering the relative rate at which the fermentation medium containing carbon substrate is added into the culture vessel. For example, in some embodiments the rate at which the carbon substrate is added to the culture vessel is less than 0.03, less than 0.02, less than 0.01, less than 0.009, less than 0.008, less than 0.007, less than 0.006, less than 0.005, less than 0.004, less than 0.003, less than 0.002, or less than 0.001 grams of carbon substrate per gram of cells (dry weight) per hour. In other embodiments, the rate at which the carbon substrate is added to the culture vessel is higher than 0.03 but less than 0.1 grams of carbon substrate per gram of cells (dry weight)per hour, such as less than 0.09, less than 0.08, less than 0.07, less than 0.06, less than 0.05, or less than 0.04 grams of carbon substrate per gram of cells (dry weight) per hour. In other embodiments, the initial supplied concentration of acetate is at least 34 grams per liter, such as 34, 35, 36, 37, 38, 39, 40, 42, 44, 46, 48, 50 or more grams per liter. The underlying goal of the methods provided herein is to continuously supply the cultured cells with ample acetate, such that the desired lipogenic processes are not limited. Accordingly, in some embodiments the amount of acetate in the culture vessel is not depleted during lipid production.

The majority of bioproduct synthesis efforts attempt to maximize cellular productivity through the engineering of metabolism, which can include genetic modifications to the cell. Though this approach can be effective, the available microbial hosts are limited due to issues surrounding available cell types that possess the required genetic manipulability. Additionally, most bioproduct synthesis efforts begin with glucose as the sole carbon substrate underlying carbon fixation. Glucose is an abundant feedstock, but has inherent drawbacks surrounding its production in large volumes without deterring food supply (see reference 30 listed below). Using a single carbon substrate also introduces issues of metabolic imbalance, resulting in surplus components. The methods describe herein circumvent these problems by introducing substrate co-feeding as a way to engineer the metabolism and products of cells. As a result, by combining the described methods of cofeeding, $CO_2$ can be fixed into acetate, which then in turn can supply the acetyl-CoA and ATP necessary for lipogenesis.

Thus, in some embodiments, $CO_2$ is converted into lipids by culturing non-photosynthetic autotrophic cells according to the methods described herein to produce acetate, and by separately culturing oleaginous cells in a culture vessel containing a fermentation medium comprising the acetate produced in by the non-photosynthetic autotrophic cells and a controlled, limiting amount of carbon substrate, to produce lipids and/or other products.

In addition to lipids, acetate can also be converted into various other bioproducts. In some embodiments, bioproducts are produced by culturing non-photosynthetic autotrophic cells according to the methods described herein to produce acetate, and separately culturing cells that utilize acetate to produce bioproducts in a culture vessel containing a fermentation medium comprising: a controlled, limiting amount of carbon substrate, and the acetate produced by the cultured non-photosynthetic autotrophic cells to produce the bioproducts. In some embodiments, the bioproducts can be any of the following: oleochemicals, polyketides, mevalonate pathway-derived natural products (e.g., terpenoids or derivatives thereof), or polyhydroxyalkanoates.

More generally, provided herein are methods in which substrate cofeeding is used to favor use by microbial cells of carbon substrates that are not (otherwise) preferentially utilized by the microbial cells, such that the carbon substrates that are not (otherwise) preferentially utilized by the microbial cells provide the majority of the carbon for carbon-based molecules produced by the microbial cells. In some embodiments, microbial cells are cultured in a culture medium that comprises a plurality of carbon substrates, wherein the mixed carbon substrates comprise at least one substrate that is preferentially utilized by the microbial cells and at least one substrate that is not preferentially utilized by the microbial cells. In this same embodiment, the at least one substrate that is preferentially utilized by the microbial cells is present in a limiting amount such that the at least one substrate that is not preferentially utilized by the microbial cells provides the majority of the carbon for carbon-based molecules produced by the microbial cells. In some embodiments, the concentration of the at least one carbon substrate that is preferentially utilized by the microbial cells is maintained in a limiting amount during the culturing of the microbial cells, such that catabolite repression is not induced.

In some embodiments, the at least one substrate that is preferentially utilized by the microbial cells is part of multi-substrate mixture, which can be a formulated multi-substrate mixture (e.g., a defined culture mixed-substrate media) or a naturally occurring multi-substrate mixture (e.g., a hemicellulosic biomass). In some embodiments, the at least one substrate that is preferentially utilized by the microbial cells is present at less than 10%, 9%, 8%, 7%, 6%, 5%, 4%, 3%, 2%, 1%, or even essentially 0%, of the total mixed carbon substrates. In some embodiments, the at least one substrate that is preferentially utilized by the microbial cells becomes accessible to the microbial cells by controlled biological, chemical, and/or thermal decomposition of a naturally occurring multi-substrate mixture, such as biomass.

In some embodiments, the at least one substrate that is preferentially utilized by the microbial cells provides NADPH and/or one or more other cofactors with reducing capabilities, such as ferredoxins, NADH, and/or $FADH_2$, to the microbial cells. In some embodiments, the at least one substrate that is preferentially utilized by the microbial cells provides ATP and/or one or more other cofactors with high-energy phosphate bond(s), such as GTP and/or pyrophosphate, to the microbial cells.

EXAMPLES

Materials and Methods
Strains and Culture Conditions

*Yarrowia lipolytica* strains based on the ACCDGA strain (MTYL065)(35) were pre-cultured at 30° C. in 14 mL test tubes containing YPD media (20 g/L glucose, 20 g/L peptone, 10 g/L yeast extract). After 24 hr, 1 mL culture was transferred to a shake flask containing 40 mL of acetate media (50 g/L sodium acetate, 1.7 g/L YNB-AA-AS, and 1.34 g/L ammonium sulfate). The shake flask culture was carried out for 24 hr to adapt the cells to acetate. Afterwards, the cells were pelleted at 18,000 g for 5 min, washed once with acetate media, and used for inoculation at an initial $OD_{600}$ of 0.05 for all *Y. lipolytica* experiments.

Mixed substrate batch cultures were carried out in shake flasks with 40 mL of acetate media except that 6 mol % of the total carbon from acetate was replaced with the supplemental substrate (glucose, fructose, glycerol, or gluconate). Continuous fed-batch supplementation cultures were carried out in 250 mL bioreactors (Applikon Biotechnology) with 150 mL working volume. Acetate media was used under batch conditions while the supplemented substrate was continuously fed at a rate of 0.13 mmol C/hr. For the acetate-only control case, the supplemented substrate was replaced with acetate and fed at the same rate to ensure that cells had equal amounts of carbon substrates throughout all conditions. All bioreactor cultures were carried out at 30° C., pH 7.0 (controlled with 10 wt % sulfuric acid), and 0.2 LPM air sparging. The dissolved oxygen levels were controlled at 20% during the growth phase and ~2% during the lipogenic phase for optimal lipid production and minimal citrate excretion(4). For gluconate $^{13}C$ tracing experiments, natural gluconate in the supplementation feed stream was replaced with [U-$^{13}C_6$]gluconate (99%, Cambridge Isotope Laboratories).

In all *Y. lipolytica* experiments having gluconate as a substrate, an ACCDGA strain overexpressing its native gluconate kinase (glucK) under the TEFin promoter was used. The expression of TEFin-glucK was performed through genome integration. This was to ensure that gluconate uptake and incorporation into central carbon metabolism was not inhibited by inadequate levels of the kinase. All other experiments were performed using the same ACCDGA strain with an empty control vector integrated into the genome. Overexpressing gluconate kinase did not have any appreciable effects on the strain's capability to produce lipids on acetate, as shown in FIG. 13.

*Moorella thermoacetica* (ATCC 39073 and 49707) were cultured in balch-type tubes containing culture medium with 8 g/L glucose, 7.5 g/L $NaHCO_3$, 7 g/L $KH_2PO_4$, 5.5 g/L $K_2HPO_4$, 2 g/L $(NH_4)_2SO_4$, 0.5 g/L $MgSO_4.7H_2O$, 0.3 g/L cysteine, 0.02 g/L $CaCl_2.2H_2O$, 1% (v/v) trace minerals (ATCC MD-TMS), and 1% (v/v) vitamins (ATCC MD-VS) at 55° C. pH 6.8. Cysteine scavenged residual dissolved oxygen in the medium(36). The headspace was pressurized to either 170 kPa with $CO_2$ or 240 kPa with 80:20 $H_2/CO_2$. For $^{13}C$ tracing experiments, natural glucose was replaced with [U-$^{13}C_6$]glucose (99%, Cambridge Isotope Laboratories) and the headspace was pressurized to 170 kPa with natural $CO_2$. The balch-tube cultures were incubated inside a strictly anoxic glovebox with magnetic stirring.

For bioreactor experiments, *M. thermoacetica* (ATCC 49707) was cultured in a strictly anoxic vessel with pH and temperature control set to 6.6 (using 10M sodium hydroxide) and 55° C. Low glucose media, which were identical to the batch culture medium except glucose concentration was either 0.13 g/L or 0.25 g/L, were continuously fed at 1.2 mL/hr or 2.3 mL/hr. The rate of effluent was the same to keep the culture volume constant at 135 mL. $H_2$ and $CO_2$ were mixed at 60:40 and sparged into the culture at 200 mL/min. The headspace pressure was maintained at 130 kPa. All the data and conditions are shown in Table 5.

Metabolite Extraction and Measurement

To extract metabolites, *Y. lipolytica* cells were collected during exponential and lipogenic phases. Cells were filtered on 0.45 μm nylon membrane filters and immediately transferred to a precooled 40:40:20 acetonitrile/methanol/water solution. After 20 minutes at −20° C., the filters were washed, and extracts were moved to Eppendorf tubes. The samples were then centrifuged for five minutes and the supernatants were dried under nitrogen.

In mid-exponential phase, the *M. thermoacetica* cultures were collected from balch-type tubes using syringes inside the anaerobic glovebox Immediately after, cellular metabolism was quenched and metabolites were extracted by quickly transferring filtered cells (on 0.2 μm nylon membrane filter) to plates containing precooled 80% acetonitrile on ice(37). After 20 minutes at 4° C., the membrane filters were washed, and the metabolite extracts were moved to Eppendorf tubes. The supernatants were obtained after five minutes of centrifugation and lyophilized.

Dried samples were re-suspended in HPLC-grade water for LC-MS analysis. These samples were analyzed on a Dionex UltiMate 3000 UPLC system (Thermo) with a ZIC-pHILIC (5 μm polymer particle) 150×2.1 mm column (EMD Millipore) coupled to a QExactive orbitrap mass spectrometer (Thermo) by electrospray ionization. With 20 mM ammonium carbonate, 0.1% ammonium hydroxide as solvent A and acetonitrile as solvent B, the chromatographic gradient was run at a flow rate of 0.150 mL/min as a linear gradient from 80% B to 20% B between 0 and 20 mins, a linear gradient from 20% B to 80% B between 20 and 20.5 mins, and 80% B held from 20.5 to 28 mins. The column and autosampler tray temperature were at 25° C. and 4° C. The mass spectrometer was operated in polarity switching mode scanning a range of 70-1,000 m/z. The resolving power was set to 70,000 for $^{13}C$ labeling experiments. With retention times determined by authenticated standards, resulting mass spectra and chromatograms were identified and processed using MAVEN software(38). To obtain labeling information of cellular bicarbonate and acetate, the labeling of carbamoyl group was obtained by comparing (i.e., computing the inverse Cauchy product) citrulline to ornithine, and the labeling of acetyl group was obtained by comparing N-acetyl-glutamate to glutamate.

Substrate Uptake and Product Secretion Measurement

For *Y. lipolytica*, 1 mL of culture was taken at each time point for media and cell dry weight (CDW) analysis. The cells were centrifuged at 18,000 g for 10 min and the supernatant was subsequently extracted, filtered (0.2 μm syringe filters), and analyzed on a high-performance liquid chromatography (HPLC). The cell pellet was then wash once with 1 mL water to remove residual media components and dried in a 60° C. oven until its mass remains unchanged. This mass was taken to be the CDW per mL of culture. As for lipids, a small volume was extracted from the culture such that it contains ~1 mg of CDW. The supernatant was discarded after centrifugation at 18,000 g for 10 min. 100 μL of an internal standard containing 2 mg/mL methyl tridecanoate (Sigma-Aldrich) and 2 mg/mL glyceryl triheptadecanoate (Sigma-Aldrich) in hexane was added to each sample. Transesterification was then carried out in 500 μL 0.5 N sodium methoxide solutions with continuous vortexing at 1200 rpm for 60 min. Afterwards, 40 μL of 98% sulfuric acid was added to neutralize the pH and 500 μL of hexane was used for extraction. Additional vortexing at 1200 rpm for 30 min was carried out and centrifugation at 6,000 g for 1 min was performed to remove cellular debris. The top hexane layer was used for analysis on a GC-FID system. All *Y. lipolytica* specific rate data were normalized to the lipid-free CDW, which was the difference between the measured CDW and the lipid titer.

For media analysis in *M. thermoacetica* cultures, small aliquots of the cultures were collected with syringes inside the anaerobic glovebox over their exponential phase. Filtered media samples (0.2 μm syringe filters) were analyzed by YSI biochemistry analyzer for glucose and by HPLC for acetate and formate along with other potential products (e.g., lactate and ethanol). Culture density was measured by spectrophotometry (0.45 gCDW L$^{-1}$ OD660$^{-1}$) at the time of sampling. The rates of substrate uptake and product secretion were determined using the rates at which substrates, products, culture density change over time. The carbon output rate for biomass was determined using growth rate and elemental biomass composition of $CH_{2.08}O_{0.53}N_{0.24}$ (39). The net $CO_2$ fixation rates were calculated based on the measured acetate and biomass carbon production rates less the corresponding measured glucose carbon consumption rates. The fraction of electrons derived from $H_2$ was inferred from the fraction of acetate and biomass carbons generated from net $CO_2$ fixation since the average oxidation state of acetate and biomass carbons is nearly the same as that of glucose.

For HPLC, 10 μL sample was injected into an Agilent 1200 High-Performance Liquid Chromatography system coupled to a G1362 Refractive Index Detector (Agilent Technologies). A Bio-Rad HPX-87H column was used for separation with 14 mM sulfuric acid as the mobile phase flowing at 0.7 mL/min. For GC-FID, 1 μL of sample was injected at a split ratio of 50:1 into an Agilent 7890B GC-FID system coupled to a J&W HP-INNOWax capillary column (Agilent Technologies). The column was held at a constant temperature of 200° C. with helium as the carrier gas (1.5 mL/min). The injection and FID temperatures were set to 260° C.

Headspace Gas Measurement

After collecting the *M. thermoacetica* cultures from balch-type tubes inside the anaerobic glovebox for intracellular and extracellular metabolite analysis, the empty balch-type tubes containing only the headspace gas were stored at 4° C. until gas chromatography-mass spectrometry (GC-MS) analysis. To measure $CO_2$ isotope labeling, 100 μl of headspace sample was collected from each tube with a gastight syringe and injected in a multimode inlet, which was maintained at 180° C., with a split of 10. Samples were analyzed on a 7890A GC system with a 60 m GS-GasPro (0.320 mm diameter) column coupled with a 5975C quadrupole mass spectrometer (Agilent). The oven was kept at 90° C. for 3 minutes before heating to 260° C. at 45° C./min and held at 260° C. for 1 minute.

Flux Balance Analysis and Isotope Tracing Flux Analysis

*M. thermoacetica* model based on the published genome-scale metabolic reconstruction(40) was employed for constraint-based flux analysis. Among the feasible metabolic flux distributions that satisfy steady-state mass balance and nutrient availability constraints, optimal solutions that maximize/minimize objective functions were obtained using the COBRA toolbox and a Gurobi solver(41). To determine $CO_2$ utilization capability, the objective was to maximize $CO_2$ consumption, or equivalently, minimize $CO_2$ production. To determine the growth potential using $H_2$ as the energy source, the objective was to maximize biomass production (i.e., cell growth). Substrate uptake and product secretion rate constraints were selected based on experimental or previously reported values.

To determine flux distributions, isotopomer mass balance constraints were also imposed based on the $^{13}C$ labeling results. For this purpose, the metabolic networks including glycolysis and PPP for *Y. lipolytica* as well as lower glycolysis, the TCA cycle, anaplerosis, the reductive acetyl-CoA pathway and the serine/glycine pathway for *M. thermoacetica* were constructed with carbon atom mapping. The labeling of following metabolites were simulated by the elementary metabolite unit (EMU) framework(42): for *Y. lipolytica*, G6P, F6P, 3PG, S7P, 6PG, R5P, PEP, and Pyr (Table 1); for *M. thermoacetica*, 3PG, PEP, Ala, acetyl-CoA, Ser, Gly, Asp, Glu, and $CO_2$ (Table 3).

The flux distribution that best simulated the metabolite labeling and uptake-secretion rates was found by minimizing the variance weighted-sum of squared residuals (SSR) between simulation and experiment:

$$\min_v \sum \left(\frac{iso_{exp} - iso(v)}{s_{iso}}\right)^2 + \sum \left(\frac{v_{exp} - v}{s_v}\right)^2$$

v and iso(v) denote in vector form the metabolic flux distribution and the simulated $^{13}C$ labeling of metabolites as a function of v. $v_{exp}$ and $iso_{exp}$ denote measured fluxes and measured metabolite labeling; $s_v$ and $s_{iso}$, their measurement standard deviation. The 95% confidence interval for each best fit flux was obtained by searching for the minimum and maximum flux values that increase the minimum SSR by less than the $\chi^2$ cutoff (1 degree of freedom) of 3.84(43).

Code Availability

The code for metabolic flux and free energy analysis is available on the GitHub public repository: https://github-.com/jopark/*moorella_yarrowia*

Example 1

Accelerating Lipogenesis from Acetate by Enhancing NADPH Generation in *Y. lipolytica*

Lipogenesis requires a balanced supply of acetyl-CoA, ATP, and NADPH at a ~1:1:2 ratio. Single substrates, such as glucose and acetate, can provide all three building blocks for lipids(16-18). However, lipid synthesis from acetate, despite its direct contribution to acetyl-CoA and ATP, is slower compared to that from glucose(19) (FIG. 1A). This is because in *Y. lipolytica* acetate-driven lipogenesis, NADPH generation is mainly through oxPPP, which takes a series of ATP-intensive reactions to arrive at staring from acetate(20).

Figure 7:
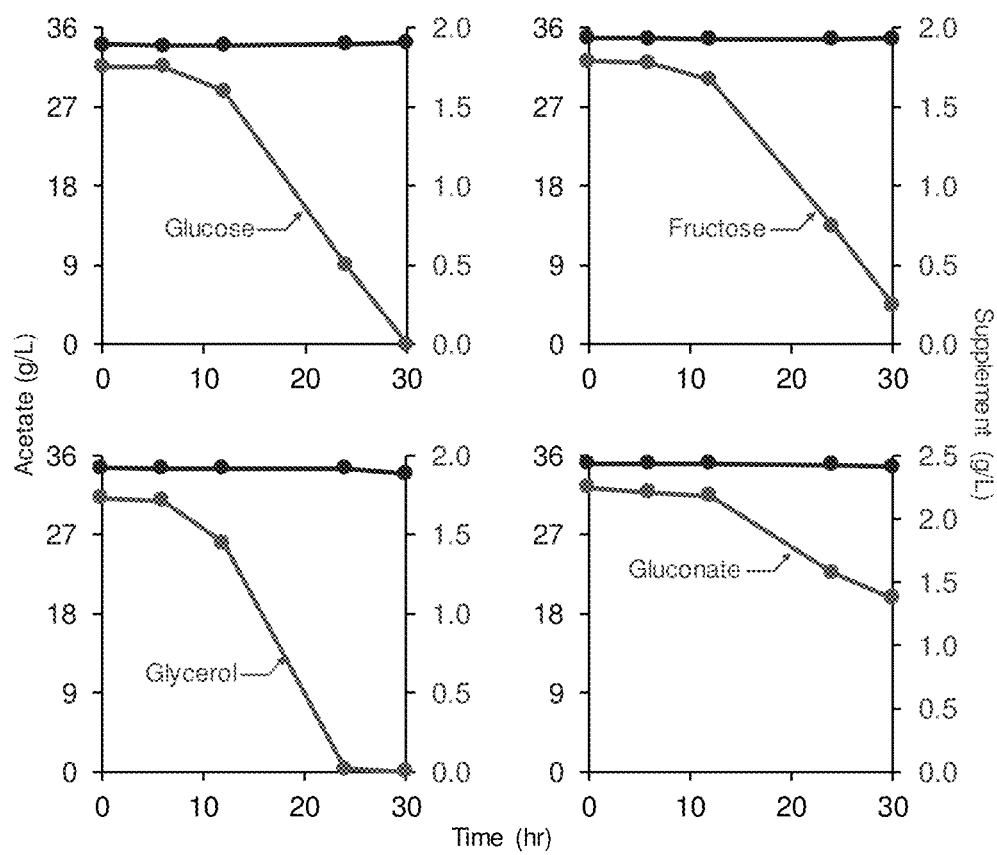
FIG. 7. Preferential consumption of glucose, fructose, glycerol, and gluconate over acetate by Y. lipolytica. Fermentations were conducted in batch cultures.

The aim of the study was to enhance acetate-to-lipid conversion by better supplying NADPH. Since glucose can flow more directly into oxPPP than acetate, both acetate and glucose were provided to a *Y. lipolytica* batch culture. Consistent with the widely accepted phenomenon of catabolite repression(21), cells consumed glucose only at first (FIG. 7). To overcome this selective preference (i.e., diauxie), a fed-batch system was devised in which the same amount of glucose was instead continuously supplied over the course of fermentation to an acetate culture (FIG. 1B). The feed rate was kept slow to maintain negligible glucose concentrations in the reactor. In this setup, despite constant feeding of glucose, simultaneous consumption of the two carbon sources was observed (FIG. 1C). Furthermore, the fed-batch cofeeding strategy enhanced both the growth and lipid production in *Y. lipolytica* significantly compared to the acetate-only control (FIG. 1D,E).

Figure 2:
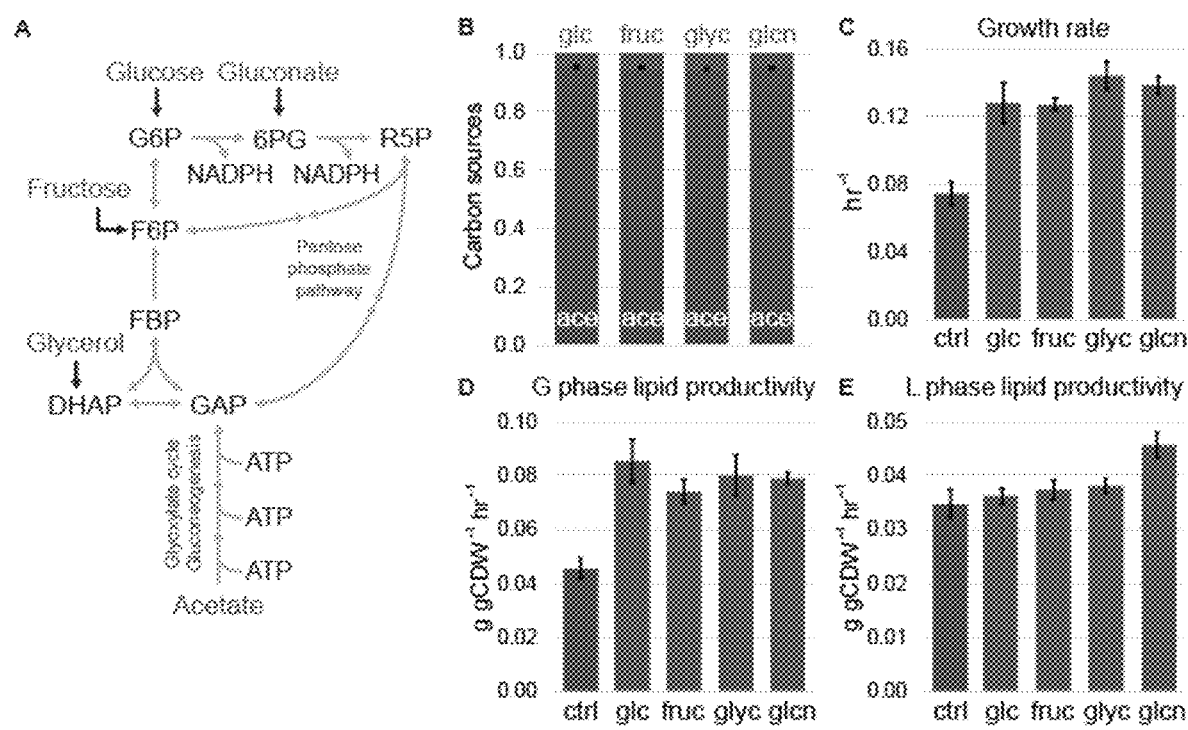
FIGS. 2A-2E. Cofeeding substrates near oxidative pentose phosphate pathway accelerates cell growth and lipogenesis from acetate.
Figure 8:
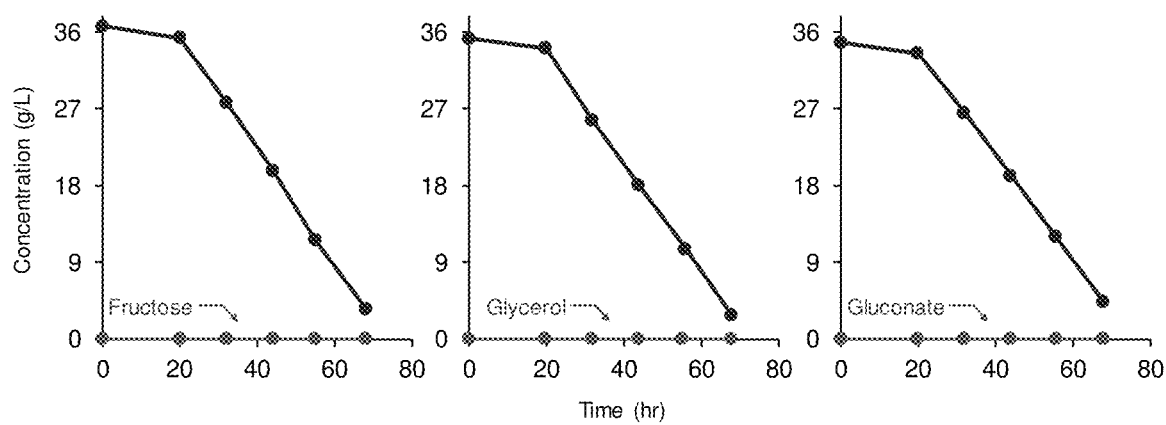
FIG. 8. Simultaneous consumption of acetate and superior substrates by Y. lipolytica. Fermentations were conducted in fed-batch cultures with the superior substrates feeding in at slow rates.
Figure 9:
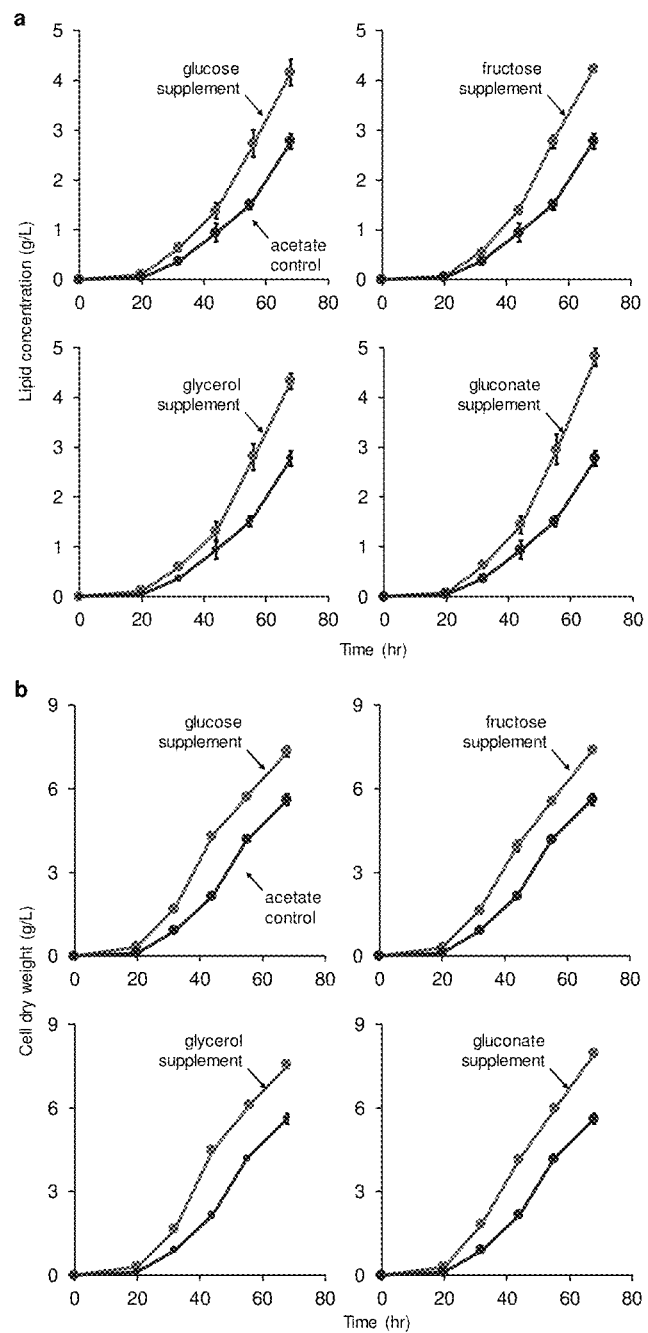
FIGS. 9A-9B. Enhanced cell growth and lipid production with substrate cofeeding in Y. lipolytica.

The same fed-batch system was used to test supplementation of other substrates (fructose, glycerol, and gluconate) that enter metabolism near oxPPP as metabolic "dopants" to provide NADPH (FIG. 2A). In all cases, a simultaneous consumption of acetate and the supplemented substrate was observed (FIG. 8). As with glucose, cell growth and lipid production were enhanced (FIG. 9) despite the supplemental substrates constituting only small fractions of carbons (FIG. 2B). To distinguish whether the increase in lipid production was due to cellular metabolism enhancements or simply having more cells in the culture, specific growth rates and productivities were determined. Substrate doping nearly doubled both the growth rate (FIG. 2C) and the specific lipid productivity during nitrogen-replete growth phase (FIG. 2D). In nitrogen-depleted lipogenic phase, glucose, fructose, and glycerol cofeeding only modestly enhanced specific productivity while gluconate cofeeding significantly outperformed all other conditions (FIG. 2E).

Example 2

NADPH-Generating Pentose Cycle

Figure 3:
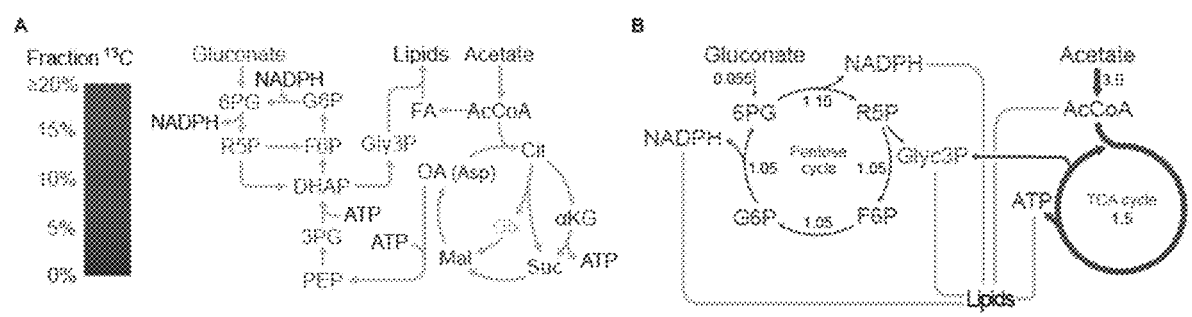
FIGS. 3A-3B. Gluconate generates NADPH via the pentose cycle.

To understand the mechanism of accelerated lipid production, the next experiments aimed to elucidate how continuous gluconate supplementation rewires metabolism. Tracing the carbons from [U-$^{13}$C$_6$]gluconate by liquid chromatography-mass spectrometry (LC-MS) resulted in the observation that the $^{13}$C atoms were confined to the PPP and upper glycolysis (FIG. 3A and Table 1). Gluconate enters metabolism as 6-phosphogluconate (6PG), which can only go in the oxidative direction through oxPPP because the combined thermodynamics of glucose-6-phosphate dehydrogenase and 6-phosphogluconolactonase ($\Delta G°=-29$ kJ/mol) strongly favors the flow of 6PG further into PPP (22). This causes gluconate to obligatorily generate NADPH via 6PG dehydrogenase, which is likely responsible for the acceleration of lipogenesis. On the other hand, metabolites in the TCA cycle as well as fatty acids were completely unlabeled, indicating exclusive contribution of lipogenic acetyl-CoA and ATP from acetate (FIG. 3A and Table 1). These labeling data suggested the partitioned usage of metabolism where acetate primarily provided acetyl-CoA and ATP while gluconate primarily provided NADPH to meet the metabolic demands of lipogenesis.

To further validate the hypothesis that gluconate enhances lipogenesis through NADPH supplementation, metabolic flux analysis using the labeling data, substrate uptake rates, and lipid production rate was performed. The flux distribution that best fit all these measurements revealed a strong flux through the oxPPP NADPH-generating steps (FIG. 3B and Table 2). Interestingly, phosphoglucose isomerase operated in the reverse direction converting fructose-6-phosphate (F6P) to glucose-6-phosphate (G6P). These results along with the non-oxPPP fluxes revealed a metabolic cycle, which was termed the "pentose cycle" (FIG. 3B and Table 2). Akin to the TCA cycle, the pentose cycle recursively oxidized the carbons from gluconate into CO$_2$ while preserving the electrons as NADPH for lipogenesis.

Example 3

Preferential Use of Glucose Leads to Excessive Decarboxylation in CO$_2$-Fixing *M. thermoacetica*

Figure 4:
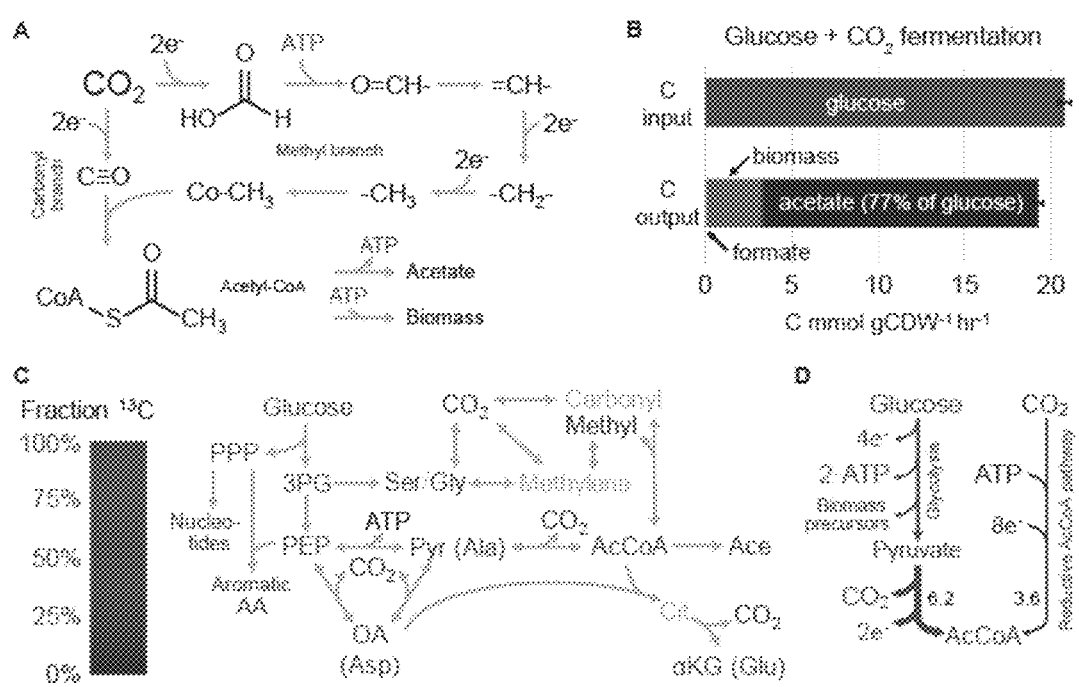
FIGS. 4A-4D. Glucose generates ATP for $CO_2$ fixation but leads to decarboxylation in *M. thermoacetica*.

In acetogenic organisms, the reductive acetyl-CoA pathway incorporates CO$_2$ as carbonyl and methyl components of the acetyl group(23) (FIG. 4B). The methyl branch of this pathway requires ATP, which acetogens may recover by acetate production. This ATP conservation contributes to efficient autotrophic CO$_2$ fixation(24), but autotrophic culture conditions, which derive energy solely from inorganic sources (e.g., oxidation of H$_2$), results in slow metabolism and low culture density(25, 26).

Since glycolysis effectively produces ATP and e$^-$ necessary for operating the reductive acetyl-CoA pathway, CO$_2$ and [U-$^{13}$C$_6$]glucose were co-fed to *M. thermoacetica* and signs of CO$_2$ incorporation were monitored. It was observed that some acetate was produced via the reductive acetyl-CoA pathway as acetate production accounted for 77% of glucose carbons, which exceeds what is possible via glycolysis (67%) (FIG. 4B). However, as glucose carbon consumption rate approximately matched the total carbon output rate of major products (i.e., biomass, acetate, and formate), no net CO$_2$ utilization was observed.

Figure 10:
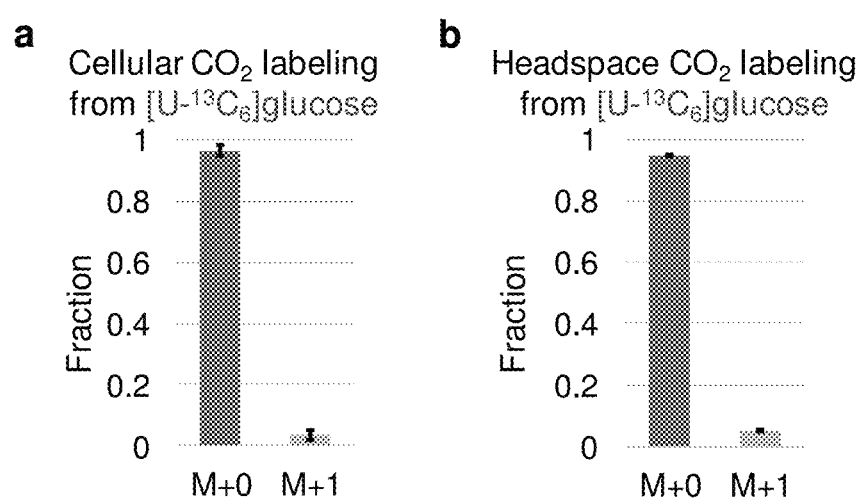
FIGS. 10A-B. Labeling of CO$_2$ in the cell and in the headspace.

It was hypothesized that no observable net CO$_2$ fixation was due to cells preferentially consuming glucose over CO$_2$. To trace the fate of $^{13}$C-glucose carbons and to visualize metabolic pathway usage, $^{13}$C enrichment in cellular metabolites was measured using LC-MS. Unlabeled CO$_2$ was provided in the headspace and CO$_2$ remained mostly unlabeled (FIG. 10). The carbons of glycolytic intermediates were ≥90% labeled except for pyruvate, which was ~50% labeled, inferred by alanine labeling (FIG. 4C, Table 3). With phosphoenolpyruvate (PEP) remaining mostly labeled, the contrasting pyruvate labeling indicated that pyruvate kinase (PEP+ADP→Pyr+ATP) was forward-driven to produce ATP.

Interestingly, serine, glycine, and other amino acids derived from pyruvate and TCA cycle intermediates were also half-labeled (FIG. 4C, Table 3). These labeling data suggested shared usage of central metabolism, where glucose and CO$_2$ jointly contributed to the TCA cycle (thus non-aromatic amino acid biosynthesis). However, because glycolysis and the pentose phosphate pathway (thus synthesis of nucleotide ribose rings and aromatic amino acids) were driven mainly by glucose, cells incorporated more carbons from glucose. Therefore, despite the simultaneous consumption of CO$_2$ and glucose, no observable net CO$_2$ fixation was the result of substrate hierarchies favoring glucose utilization, which subsequently led to pyruvate decarboxylation via pyruvate:ferredoxin oxidoreductase (FIG. 4D, Table 4), and CO$_2$-producing biosynthetic pathways (FIG. 11) that together outpaced CO$_2$ incorporation.

Example 4

Figure 5:
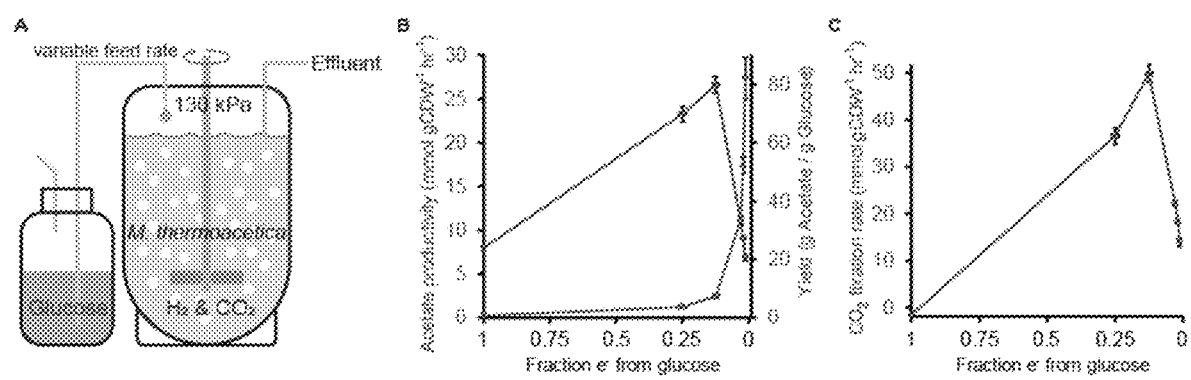
FIGS. 5A-5C. Continuous glucose cofeeding accelerates acetogenesis from $CO_2$ fixation at the autotrophic limit.
Figure 12:
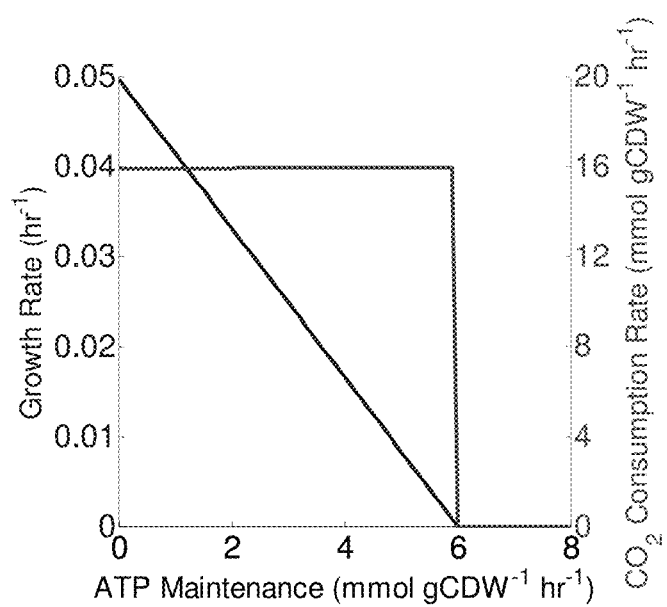
FIG. 12. M. thermoacetica growth rate decreases with increasing ATP demand while CO$_2$ consumption drops suddenly to 0 once ATP demand reaches the threshold of ATP generation capability. Using the genome-scale metabolic model, we probed cell growth and CO$_2$ utilization rates with increasing ATP demand The maximum growth objective function was used. As ATP cell maintenance cost is the only ATP requirement for converting CO$_2$ into acetate via the reductive acetyl-CoA pathway, we observed that CO$_2$ consumption remained steady until ATP cell maintenance demand reached ATP generation capability.

Accelerating Acetate Production from CO$_2$ by Decoupling e$^-$ Supply from Decarboxylation As e$^-$ generation from glucose is coupled to glycolytic ATP production and pyruvate decarboxylation, the aim was to decouple e$^-$ generation and to make net CO$_2$ incorporation more favorable and dominant Since acetate production via the reductive acetyl-CoA pathway does not consume ATP, cell maintenance (e.g., housekeeping) is the only ATP requirement for converting $CO_2$ to acetate (FIG. 12). Hence, a glucose-limiting culture environment was designed in a chemostat to supply sufficient amounts of ATP through glycolysis without subsequent decarboxylation (FIG. 5A). To compensate for the decreased e$^-$ availability, cells were provided with $H_2$ as a carbon-free e$^-$ source that yields reducing agents without $CO_2$ generation. Low dilution rates (0.009 and 0.017 hr$^{-1}$) were selected to minimize biomass formation and maximize cell residence time in the reactor.

Using this glucose doping system, productivities and yields at various fractions of electrons derived from glucose versus $H_2$ were obtained (FIG. 5B). At steady state, acetate concentration in the effluent could exceed 13 g/L. With decreasing fractions of electrons from glucose, acetate production rate could be more than 80 times as fast as the glucose feed rate, and the carbon yield monotonically increased to >80 g acetate produced per g glucose consumed. This high yield indicated that the overwhelming majority of acetate and biomass was derived from $CO_2$ rather than glucose. While cell growth rates were slow in the chemostat (growth rate=dilution rate), acetate production remained substantial (FIG. 5B).

Across the glucose+$H_2$ energy landscape, $CO_2$ fixation rates peaked at 50 mmol gCDW$^{-1}$ hr$^{-1}$ (2.2 g gCDW$^{-1}$ hr$^{-1}$) (FIG. 5C). Such high rates implied that the method not only minimized $CO_2$ generation from pyruvate decarboxylation but also increased the reductive acetyl-CoA pathway flux. Furthermore, the maximum rate at an interior point between the two extremes (glucose-only and $H_2$-only) demonstrated that $CO_2$ fixation rate is determined by balancing the production of reducing agents and ATP from $H_2$ and glucose, respectively. Thus, by glucose doping, e$^-$ supply was decoupled from decarboxylation, cellular metabolism was shifted towards favoring $CO_2$ utilization over glucose, and rapid and continuous $CO_2$ conversion into acetate was achieved.

Example 5

Coordination of "Doped" Acetogenesis and Lipogenesis

Figure 6:
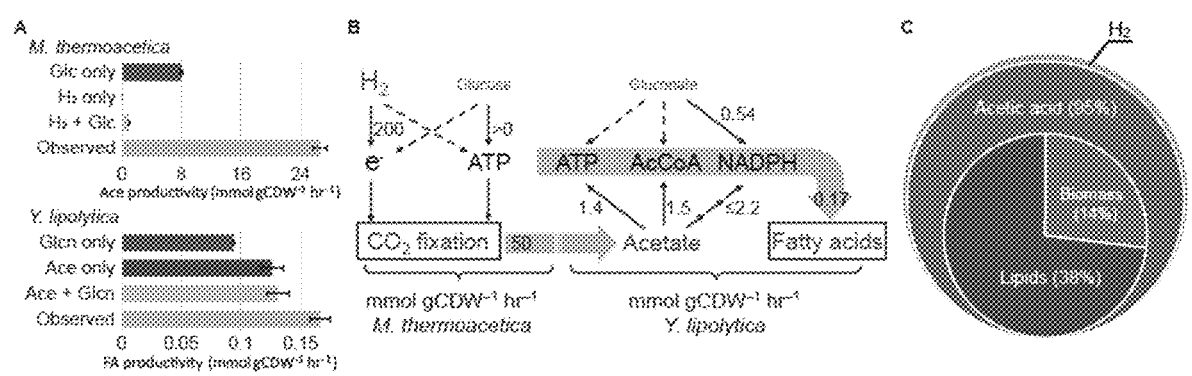
FIGS. 6A-6C. Synergy and coordination of substrate cofeeding accelerate the conversion of CO$_2$ and H$_2$ into lipids.

Coordinating acetogenesis and lipogenesis, which the present substrate cofeeding strategies accelerated, allows $CO_2$-to-acetate-to-lipid conversion. Interestingly, the observed acetate and fatty acid productivities from glucose- and gluconate-doping ($V_{12}$) exceeded not only the measured productivities with individual substrate feeding ($V_1$ or $V_2$) but also the expected rates for substrate cofeeding ($V_1+V_2$) (FIG. 6A). The expected rates were linearly extrapolated from the combination of supplemental glucose feeding with $CO_2$+$H_2$ batch fermentation for acetogenesis and the combination of supplemental gluconate feeding with acetate batch fermentation for lipogenesis.

The observed synergy ($V_{12}$>$V_1+V_2$) was attributed to complementary substrate cofeeding. While the performed $^{13}$C labeling experiments showed the roles of glucose and gluconate in cofactor synthesis, the theoretical framework that illustrates the feasibility of this synergy was still undefined. To this end, stoichiometric analysis of the different fates of individual substrates was combined with experimentally measured rates of single-substrate acetogenesis and lipogenesis. The maximum carbon, electron, and ATP attainable with mixed substrates were then evaluated for the two processes. It was identified that the ATP and NADPH generation by glucose and gluconate doping relieved the limiting ingredients for acetate and lipid synthesis, respectively, and, in conjunction with the primary substrates, better balanced the energy and cofactor ratio requirements (FIG. 6B).

Ultimately, dilute acetate (<40 g/L) was converted to and enriched as lipids in Y. lipolytica cells for ease of separation. In terms of organic carbon yield, the integrated acetogenesis-lipogenesis process converted 1 g of glucose to ~13 g of lipids (0.154 g lipids/g acetate×~82 g acetate/g glucose) by extensive $CO_2$ utilization. Increasing mass transfer rates of gases improves $H_2$ (and $CO_2$) utilization efficiency, and it has been reported that ~95% of supplied $H_2$ can be used by commercial $CO_2$-fixing microbes(27, 28). By continuously converting $CO_2$ and $H_2$ to lipids via coordinated acetogenesis and lipogenesis, 38% of energy from $H_2$ was stored as lipids and 14% as yeast biomass (FIG. 6C). Nearly all carbons (99%) in lipids originated from $CO_2$.

Calculation of Specific Growth Rate and Productivities

Y. lipolytica batch fermentations have two distinct phases: (a) nitrogen replete growth phase (6-44 hr) and (b) nitrogen deplete lipogenic phase (44 hr onwards). During the growth phase, exponential growth takes place while during the lipogenic phase, cell division ceases due to nitrogen limitation.

For the growth phase, an exponential curve was fitted through the lipid-free CDW measurements during the 20 and 32 hr time points and the exponent was taken as the specific growth rate $\mu$ (hr$^{-1}$). To obtain the specific productivity, the ratio between lipid synthesis and lipid-free CDW synthesis was calculated using the lipid titer and lipid-free CDW measurements at the 20 and 32 hr time points. This ratio was then multiplied by $\mu$ to obtain the specific lipid productivity normalized to lipid-free CDW $q_{lipid,G}$ (g gCDW$^{-1}$ hr$^{-1}$).

As for the lipogenic phase, the cell number and hence the lipid-free CDW was approximately constant. Specific lipid productivity was calculated by first determining the volumetric lipid production rate using the lipid titer measurements at the 56 and 68 hr time points. This rate was then divided by the lipid-free CDW measured at the end-point of the fermentation to obtain the specific productivity $q_{lipid,L}$ (g gCDW$^{-1}$ hr$^{-1}$).

Genome-Scale Stoichiometric Metabolic Model

The present genome-scale model of M. thermoacetica (iAI563) contains 563 genes and 712 reactions. Six new reactions and 5 new genes involved in ethanol metabolism into iAI558 were incorporated(Table 6). Balancing electrons in the reactions that involve ferredoxin, iAI563 includes corrected stoichiometries (Table 7).

Relationship between ATP Availability and $CO_2$ Fixation

In autotrophic growth with an electron-rich energy source such as $H_2$, cells produce ATP with energy derived from transmembrane proton motive force(26). Using the genome-scale metabolic model, the electron-rich metabolism in $H_2$+$CO_2$ gas fermentation was characterized. The maximum $H_2$ consumption rate was set to 32 mmol gCDW$^{-1}$ hr$^{-1}$ (selected based on the specific hydrogenase activity and the assumption that hydrogenase could take up to 1% of total protein mass). With the objective function of maximum growth, it was found that increasing ATP consumption (by increasing the non-growth associated ATP maintenance requirement) produced decreasing growth rate without affecting the consumption rate of the oxidizing agent and carbon source $CO_2$ (FIG. 12). This suggested that rapid $CO_2$ fixation is feasible as long as minimum cellular ATP requirement is met.

Analysis of Synergies Associated with Substrate Cofeeding

Using the measured product synthesis rates with individual substrates, the extent of synergies by comparing the measured product synthesis rates with expected product synthesis rates were evaluated when two substrates were provided. Since the preferred substrate feeds (glucose and gluconate) were controlled, the supplement of those were linearly extrapolated using their contribution in metabolism as the increase in productivities.

For *Y. lipolytica*, the lipogenic phase was chosen, in which gluconate contributed to ~5.2% of carbon uptake, and the following was observed:

|  | Fatty acid productivity (mmol gCDW$^{-1}$ hr$^{-1}$) |
|---|---|
| Acetate | 0.126 |
| Gluconate | 0.094 |
| Acetate + Gluconate | 0.126 + 0.052 × |
| Expected | 0.094 = 0.13 |
| Observed | 0.166 ± 0.008 |

For *M. thermoacetica*, the maximum acetate productivity condition was chosen, in which glucose contributed to ~12.4% of electron uptake, and the following was obtained:

|  | Acetate productivity (mmol gCDW$^{-1}$ hr$^{-1}$) |
|---|---|
| H$_2$ & CO$_2$ | ~0 |
| Glucose & CO$_2$ | 8.00 |
| H$_2$ + Glucose & CO$_2$ Expected | 0 + 0.124 × 8.00 = 0.99 |
| Observed | 26.6 ± 0.9 |

The experiments focused on determining the feasibility of the observed synergies with substrate cofeeding. It was hypothesized that the synergies were due to complementary roles of different substrates in providing balanced ingredients for lipogenesis and acetogenesis. One fatty acid (FA 18:0) molecule synthesis requires 18 carbons (i.e., 9 acetyl groups), 8 ATP, and 16 NADPH. Acetate and gluconate each can generate these three ingredients. For acetogenesis, one acetate molecule synthesis requires 2 CO$_2$ and 4 reducing equivalents (8 s$^-$). Both H$_2$ and glucose generate reducing equivalents for CO$_2$ reduction. As *Y. lipolytica* and *M. thermoacetica* cell maintenance (housekeeping) requires ATP, the synthesis of fatty acid and acetate actually requires greater than 8 and 0 ATPs, respectively.

While individual substrates can satisfy these metabolic requirements, their product synthesis rates are different. It was hypothesized that these rates are mainly determined by the synthesis of those ingredients that are least accessible by cells. In other words, if more pathway steps are required to synthesize the precursors, they are likely rate determining because of greater protein burdens and greater likelihood of containing rate-limiting enzymatic steps.

The formulation of the analysis of metabolic requirements and burdens began by identifying different substrate usage pathways, their output products, and the number of enzymatic steps.

For *Y. lipolytica*:

| Cases | Carbon | ATP | NADPH | # Steps | Role | Flux (mmol gCDW$^{-1}$ hr$^{-1}$) |
|---|---|---|---|---|---|---|
| Ace#1 | 2 | −2 | 0 | 1 | Max Carbon | 1.14 |
| Ace#2 | 0 | 8 | 0 | 9 | Max ATP | 0.49 |
| Ace#3 | 0 | −1 | 3 | 74 | Max NADPH | 0.67 |
| Glcn#1 | 3.33 | 10 | 1 | 16 | Max Carbon | 0.51 |
| Glcn#2 | 0 | 26.67 | 1 | 29.33 | Max ATP | 0 |
| Glcn#3 | 0 | −1 | 11 | 37 | Max NADPH | 0.090 |
| FA 18:0 | 18 | >8 | 16 |  |  |  |

These stoichiometries represent the numbers of products and steps when one acetate or gluconate goes through different pathways. These different cases can be linearly combined to satisfy metabolic demands for FA 18:0 synthesis, and the calculations sought to determine their usage in terms of fluxes. Mathematically, these problems were solved by linear programming, with the aim of finding a positive flux vector that i) minimizes enzymatic steps, ii) produces exact moles of Carbon and NADPH (reducing equivalents) required for product synthesis, and iii) produces ATP greater than the requirement for product synthesis. The mathematical formulation is presented below.

$$\min[\,0\ \ 8\ \ 73\,]\begin{bmatrix} Ace\#1 \\ Ace\#2 \\ Ace\#3 \end{bmatrix}$$

such that $$\begin{bmatrix} 2 & 0 & 0 \\ 0 & 0 & 3 \end{bmatrix} \begin{bmatrix} Ace\#1 \\ Ace\#2 \\ Ace\#3 \end{bmatrix} = \begin{bmatrix} 18 \\ 16 \end{bmatrix},$$

$$[\,-2\ \ 8\ \ -1\,]\begin{bmatrix} Ace\#1 \\ Ace\#2 \\ Ace\#3 \end{bmatrix} \geq 8, \text{ and}$$

$$\begin{bmatrix} Ace\#1 \\ Ace\#2 \\ Ace\#3 \end{bmatrix} \geq 0$$

For acetate:
To get absolute fluxes, the solution vector was multiplied by the measured lipid production rate from acetate, 0.126 mmol gCDW$^{-1}$ hr$^{-1}$:

$$fluxes_{Ace} = 0.126 \begin{bmatrix} Ace\#1 \\ Ace\#2 \\ Ace\#3 \end{bmatrix}$$

For gluconate:

$$\min[\,15\ \ 28.33\ \ 36\,]\begin{bmatrix} Glcn\#1 \\ Glcn\#2 \\ Glcn\#3 \end{bmatrix}$$

such that $$\begin{bmatrix} 3.33 & 0 & 0 \\ 1 & 1 & 11 \end{bmatrix} \begin{bmatrix} Glcn\#1 \\ Glcn\#2 \\ Glcn\#3 \end{bmatrix} = \begin{bmatrix} 18 \\ 16 \end{bmatrix},$$

$$\begin{bmatrix} 10 & 26.67 & -1 \end{bmatrix} \begin{bmatrix} Glcn\#1 \\ Glcn\#2 \\ Glcn\#3 \end{bmatrix} \geq 8, \text{ and}$$

$$\begin{bmatrix} Glcn\#1 \\ Glcn\#2 \\ Glcn\#3 \end{bmatrix} \geq 0$$

To get absolute fluxes, the solution vector was multiplied by the measured lipid production rate from gluconate, 0.094 mmol gCDW$^{-1}$ hr$^{-1}$:

$$fluxes_{Glcn} = 0.094 \begin{bmatrix} Glcn\#1 \\ Glcn\#2 \\ Glcn\#3 \end{bmatrix}$$

The resulting flux values are shown in italics in the last column of the table above. For each nutrient, these fluxes were used to define the flux upper bound (U.B.) of each case by summing all the fluxes of those cases whose enzymatic steps are greater and the scaled-back fluxes (proportionally by the ratios of enzymatic steps so as not to increase total protein burden) of those cases whose enzymatic steps are less. These upper bounds correspond to the maximum rates of substrate utilization through corresponding cases.

| Cases | U.B. (mmol gCDW$^{-1}$ hr$^{-1}$) |
|---|---|
| Ace#1 | 1.14 + 0.49 + 0.67 |
| Ace#2 | 1.14 × 1/9 + 0.49 + 0.67 |
| Ace#3 | 1.14 × 1/74 + 0.49 × 9/74 + 0.67 |
| Glcn#1 | 0.51 + 0 + 0.090 |
| Glcn#2 | 0.51 × 16/29.33 + 0 + 0.090 |
| Glcn#3 | 0.51 × 16/37 + 0 + 0.090 |

These upper bounds were used to test the feasibility of the observed synergy between acetate and gluconate. Gluconate feed was controlled at 0.049 mmol gCDW$^{-1}$ hr$^{-1}$, which is well below the limits for Glcn #1, Glcn #2, and Glcn #3. Therefore, 0.049 mmol gCDW$^{-1}$ hr$^{-1}$ was used as the upper bound for the sum of all gluconate utilization cases.

To obtain maximum Carbon for FA 18:0 synthesis:

$$\max f_c = \begin{bmatrix} 2 & 0 & 0 & 3.33 & 0 & 0 \end{bmatrix} \begin{bmatrix} Ace\#1 \\ Ace\#2 \\ Ace\#3 \\ Glcn\#1 \\ Glcn\#2 \\ Glcn\#3 \end{bmatrix}$$

To obtain maximum ATP for FA 18:0 synthesis:

$$\max f_{ATP} = \begin{bmatrix} -2 & 8 & -1 & 10 & 26.67 & -1 \end{bmatrix} \begin{bmatrix} Ace\#1 \\ Ace\#2 \\ Ace\#3 \\ Glcn\#1 \\ Glcn\#2 \\ Glcn\#3 \end{bmatrix}$$

To obtain maximum NADPH for FA 18:0 synthesis:

$$\max f_{NADPH} = \begin{bmatrix} 0 & 0 & 3 & 1 & 1 & 11 \end{bmatrix} \begin{bmatrix} Ace\#1 \\ Ace\#2 \\ Ace\#3 \\ Glcn\#1 \\ Glcn\#2 \\ Glcn\#3 \end{bmatrix}$$

which are all subject to:

$$\begin{bmatrix} 0 & 0 & 0 & 1 & 1 & 1 \end{bmatrix} \begin{bmatrix} Ace\#1 \\ Ace\#2 \\ Ace\#3 \\ Glcn\#1 \\ Glcn\#2 \\ Glcn\#3 \end{bmatrix} \leq 0.049, \text{ and}$$

$$0 \leq \begin{bmatrix} Ace\#1 \\ Ace\#2 \\ Ace\#3 \\ Glcn\#1 \\ Glcn\#2 \\ Glcn\#3 \end{bmatrix} \leq \begin{bmatrix} 2.30 \\ 1.29 \\ 0.75 \\ 0.049 \\ 0.049 \\ 0.049 \end{bmatrix}$$

The following maximum fluxes (mmol gCDW$^{-1}$ hr$^{-1}$) were obtained:

$f_c$=4.77, $f_{ATP}$=11.66, and $f_{NADPH}$=2.78

Corresponding maximum FA 18:0 synthesis rates (mmol gCDW$^{-1}$ hr$^{-1}$) are obtained by dividing these fluxes by stoichiometric requirements:

$f_c/18$=0.27, $f_{ATP}/8$=1.46, and $f_{NADPH}/16$=0.17

Since the limiting component (i.e., NADPH) determines the rate of fatty acid synthesis, the minimum of these was taken to obtain the maximum FA 18:0 productivity of 0.17 mmol gCDW$^{-1}$ hr$^{-1}$. This value is similar to the observed fatty acid synthesis of 0.166±0.008 mmol gCDW$^{-1}$ hr$^{-1}$ from acetate with gluconate doping. Thus, it was concluded that the observed synergy is theoretically feasible.

For *M. thermoacetica*:

| Cases | ATP | Reducing eqv. (2e⁻) | Acetate | Pyruvate | # Steps | Role | Flux (mmol gCDW⁻¹ hr⁻¹) |
|---|---|---|---|---|---|---|---|
| H₂#1 | 0.125 | 1 | 0 | 0 | 3 | Max ATP | ~0 |
| H₂#2 | 0 | 1 | 0 | 0 | 1 | Fastest | Mass transfer rate (R) |
| Glc#1 | 2 | 2 | 0 | 2 | 15 | Max efficiency | 0.80 |
| Glc#2 | 4 | 0 | 3 | 0 | 31 | Max ATP | 2.67 |
| Ace | >0 | 4 | | | | | |

These stoichiometries represent the numbers of products and steps when one $H_2$ or glucose goes through different pathways. The microbial utilization of $H_2$ is widely accepted to be mass transfer limited. However, since the appreciable acetate production or cell growth in an autotrophic condition with $H_2$ and $CO_2$ was not observed, 0 flux was assigned for the ATP-producing $H_2$ #1 case. Glc #1 and Glc #2 fluxes were obtained from the observed glucose uptake under glucose+$CO_2$ fermentation and cells' acetate yield. Glucose uptake was 3.47 mmol gCDW⁻¹ hr⁻¹ and acetate yield was 77%. Therefore, Glc #2 was computed to be 3.47× 0.77=2.67. Glc #1 was approximated as the rest of glucose flux: 3.47−2.67=0.80. Glc #1 represents maximum ATP efficiency: the number of ATP produced per step. Flux upper bounds were computed by summing all the fluxes of those cases whose enzymatic steps are greater and the scaled-back fluxes (proportionally by the ratios of enzymatic steps so as not to increase total protein burden) of those cases whose enzymatic steps are less.

| Cases | U.B. (mmol gCDW⁻¹ hr⁻¹) |
|---|---|
| H2#1 | 0 + R × ⅓ |
| H2#2 | R + 0 |
| Glc#1 | 2.67 + 0.80 |
| Glc#2 | 2.67 + 0.80 × 15/31 |

Mathematically, the calculations aimed to find a positive flux vector that i) minimizes enzymatic steps, ii) produces reducing equivalents required for one acetate production, and iii) produces ATP greater than the requirement for product synthesis (i.e., >0). The mathematical formulation is as follows:

$$\min [3 \ 1 \ 15 \ 31] \begin{bmatrix} H_2\#1 \\ H_2\#2 \\ Glc\#1 \\ Glc\#2 \end{bmatrix}$$

such that $$[1 \ 1 \ 2 \ 0] \begin{bmatrix} H_2\#1 \\ H_2\#2 \\ Glc\#1 \\ Glc\#2 \end{bmatrix} = 4,$$

$$[0.125 \ 0 \ 2 \ 4] \begin{bmatrix} H_2\#1 \\ H_2\#2 \\ Glc\#1 \\ Glc\#2 \end{bmatrix} \geq \varepsilon, \text{ and}$$

$$0 \leq \begin{bmatrix} H_2\#1 \\ H_2\#2 \\ Glc\#1 \\ Glc\#2 \end{bmatrix} \leq \begin{bmatrix} R/3 \\ R \\ 3.06 \\ 3.47 \end{bmatrix}$$

$\varepsilon$ represents an infinitesimally small positive number. When sufficient $H_2$ is provided to the system (R>4), we get the following solution:

$H_2$ #1=0, $H_2$ #2=4-$\varepsilon$/2, Glc #1>0, and Glc #2=0

This solution represents that since $H_2$ #2 and Glc #1 have fewer steps, cells in chemostat would be inclined to use $H_2$ #2 for reducing power generation and Glc #1 for ATP generation. The described glucose cofeeding system supplied <3.06 mmol gCDW⁻¹ hr⁻¹, and thus, the Glc #1 flux would be the glucose feeding rate. Therefore, maximization of acetate production can be achieved as long as ATP is generated by glucose doping and gas mass transfer (R) is maximized, and the maximum acetate productivity (~R/4) would be proportional to $H_2$ transfer rate.

REFERENCES

1. R. Ledesma-Amaro, J. M. Nicaud, Metabolic Engineering for Expanding the Substrate Range of Yarrowia lipolytica. *Trends Biotechnol* 34, 798 (October 2016).
2. S. Atsumi, T. Hanai, J. C. Liao, Non-fermentative pathways for synthesis of branched-chain higher alcohols as biofuels. *Nature* 451, 86 (2008).
3. Z. Xue et al., Production of omega-3 eicosapentaenoic acid by metabolic engineering of *Yarrowia lipolytica*. *Nat Biotechnol* 31, 734 (August 2013).
4. K. J. Qiao, T. M. Wasylenko, K. Zhou, P. Xu, G. Stephanopoulos, Lipid production in *Yarrowia lipolytica* is maximized by engineering cytosolic redox metabolism. *Nature biotechnology* 35, 173 (February 2017).
5. A. Kita et al., Development of genetic transformation and heterologous expression system in carboxydotrophic thermophilic acetogen Moorella thermoacetica. *J Biosci Bioeng* 115, 347 (April 2013).
6. J. Monod, Recherches sur la croissance des cultures bacteriennes. (1942).
7. L. Aristilde, I. A. Lewis, J. O. Park, J. D. Rabinowitz, Hierarchy in Pentose Sugar Metabolism in *Clostridium Acetobutylicum*. *Appl Environ Microbiol*, (Dec. 19, 2014).
8. B. Goerke, J. Stulke, Carbon catabolite repression in bacteria: many ways to make the most out of nutrients. *Nat Rev Microbiol* 6, 613 (August 2008).
9. A. Bren et al., Glucose becomes one of the worst carbon sources for *E. coli* on poor nitrogen sources due to suboptimal levels of cAMP. *Sci Rep* 6, 24834 (Apr. 25, 2016).
10. C. J. Joshua, R. Dahl, P. I. Benke, J. D. Keasling, Absence of diauxie during simultaneous utilization of glucose and Xylose by Sulfolobus acidocaldarius. *J Bacteriol* 193, 1293 (March 2011).
11. R. Hermsen, H. Okano, C. You, N. Werner, T. Hwa, A growth-rate composition formula for the growth of *E. coli* on co-utilized carbon substrates. *Mol Syst Biol* 11, 801 (Apr. 9, 2015).
12. K. Martinez et al., Coutilization of glucose and glycerol enhances the production of aromatic compounds in an *Escherichia coli* strain lacking the phosphoenolpyruvate: carbohydrate phosphotransferase system. *Microb Cell Fact* 7, 1 (Jan. 22, 2008).

13. R. Garcia Sanchez et al., Improved xylose and arabinose utilization by an industrial recombinant Saccharomyces cerevisiae strain using evolutionary engineering. *Biotechnol Biofuels* 3, 13 (Jun. 15, 2010).
14. S. M. Kim et al., Simultaneous utilization of glucose and xylose via novel mechanisms in engineered *Escherichia coli*. *Metab Eng* 30, 141 (July 2015).
15. G. Bowes, R. H. Hageman, W. L. Ogren, Light Saturation, Photosynthesis Rate, Rudp Carboxylase Activity, and Specific Leaf Weight in Soybeans Grown under Different Light Intensities. *Crop Sci* 12, 77 (1972).
16. J. Xu, N. Liu, K. Qiao, S. Vogg, G. Stephanopoulos, Application of metabolic controls for the maximization of lipid production in semicontinuous fermentation. *Proc Natl Acad Sci USA* 114, E5308 (Jul. 3, 2017).
17. C. Ratledge, J. P. Wynn, The biochemistry and molecular biology of lipid accumulation in oleaginous microorganisms. *Advances in applied microbiology* 51, 1 (2002).
18. K. Qiao et al., Engineering lipid overproduction in the oleaginous yeast *Yarrowia lipolytica*. *Metab Eng* 29, 56 (May, 2015).
19. P. Fontanille, V. Kumar, G. Christophe, R. Nouaille, C. Larroche, Bioconversion of volatile fatty acids into lipids by the oleaginous yeast *Yarrowia lipolytica*. *Bioresource Technology* 114, 443 (2012/06/01/, 2012).
20. N. Liu, K. Qiao, G. Stephanopoulos, (13)C Metabolic Flux Analysis of acetate conversion to lipids by *Yarrowia lipolytica*. *Metab Eng* 38, 86 (November 2016).
21. J. M. Gancedo, Carbon catabolite repression in yeast. *Eur J Biochem* 206, 297 (Jun. 1, 1992).
22. J. P. Casazza, R. L. Veech, The Interdependence of Glycolytic and Pentose Cycle Intermediates in Ad-Libitum Fed Rats. *J Biol Chem* 261, 690 (Jan. 15, 1986).
23. S. W. Ragsdale, E. Pierce, Acetogenesis and the Wood-Ljungdahl pathway of CO(2) fixation. *Biochimica et biophysica acta* 1784, 1873 (December 2008).
24. A. Mall et al., Reversibility of citrate synthase allows autotrophic growth of a thermophilic bacterium. *Science* 359, 563 (2018).
25. T. Nunoura et al., A primordial and reversible TCA cycle in a facultatively chemolithoautotrophic thermophile. *Science* 359, 559 (2018).
26. K. Schuchmann, V. Muller, Autotrophy at the thermodynamic limit of life: a model for energy conservation in acetogenic bacteria. *Nat Rev Microbiol* 12, 809 (December 2014).
27. J. Daniell, M. Kopke, S. Simpson, Commercial Biomass Syngas Fermentation. *Energies* 5, 5372 (2012).
28. P. Hu, H. Rismani-Yazdi, G. Stephanopoulos, Anaerobic CO2 fixation by the acetogenic bacterium *Moorella thermoacetica*. *AIChE Journal* 59, 3176 (2013).
29. J. Blazeck et al., Harnessing *Yarrowia lipolytica* lipogenesis to create a platform for lipid and biofuel production. *Nat Commun* 5, 3131 (2014).
30. S. N. Naik, V. V. Goud, P. K. Rout, A. K. Dalai, Production of first and second generation biofuels: A comprehensive review. *Renewable and Sustainable Energy Reviews* 14, 578 (2010/02/01/, 2010).
31. S. L. Daniel, T. Hsu, S. I. Dean, H. L. Drake, Characterization of the H2- and CO-dependent chemolithotrophic potentials of the acetogens *Clostridium thermoaceticum* and *Acetogenium kivui*. *J Bacteriol* 172, 4464 (August 1990).
32. R. Ledesma-Amaro, R. Dulermo, X. Niehus, J. M. Nicaud, Combining metabolic engineering and process optimization to improve production and secretion of fatty acids. *Metab Eng* 38, 38 (November 2016).
33. V. J. J. Martin, D. J. Pitera, S. T. Withers, J. D. Newman, J. D. Keasling, Engineering a mevalonate pathway in *Escherichia coli* for production of terpenoids. *Nature biotechnology* 21, 796 (July 2003).
34. C. A. Haynes, R. Gonzalez, Rethinking biological activation of methane and conversion to liquid fuels. *Nat Chem Biol* 10, 331 (May, 2014).
35. M. Tai, G. Stephanopoulos, Engineering the push and pull of lipid biosynthesis in oleaginous yeast *Yarrowia lipolytica* for biofuel production. *Metab Eng* 15, 1 (January 2013).
36. L. Michaelis, E. S. G. Barron, Oxidation-reduction systems of biological significance. II. Reducing effect of cysteine induced by free metals. *J Biol Chem* 81, 29 (January 1929).
37. J. D. Rabinowitz, E. Kimball, Acidic acetonitrile for cellular metabolome extraction from *Escherichia coli*. *Anal Chem* 79, 6167 (Aug. 15, 2007).
38. M. F. Clasquin, E. Melamud, J. D. Rabinowitz, LC-MS data processing with MAVEN: a metabolomic analysis and visualization engine. *Current protocols in bioinformatics/editoral board, Andreas D. Baxevanis . . . [et al.]* Chapter 14, Unit 14 11 (March 2012).
39. B. P. Tracy, S. W. Jones, A. G. Fast, D. C. Indurthi, E. T. Papoutsakis, *Clostridia*: the importance of their exceptional substrate and metabolite diversity for biofuel and biorefinery applications. *Curr Opin Biotech* 23, 364 (June 2012).
40. M. A. Islam, K. Zengler, E. A. Edwards, R. Mahadevan, G. Stephanopoulos, Investigating *Moorella thermoacetica* metabolism with a genome-scale constraint-based metabolic model. *Integr Biol* (Camb) 7, 869 (August 2015).
41. J. Schellenberger et al., Quantitative prediction of cellular metabolism with constraint-based models: the COBRA Toolbox v2.0. *Nat Protoc* 6, 1290 (September 2011).
42. M. R. Antoniewicz, J. K. Kelleher, G. Stephanopoulos, Elementary metabolite units (EMU): A novel framework for modeling isotopic distributions. *Metab Eng* 9, 68 (January 2007).
43. M. R. Antoniewicz, J. K. Kelleher, G. Stephanopoulos, Determination of confidence intervals of metabolic fluxes estimated from stable isotope measurements. *Metab Eng* 8, 324 (July 2006).

TABLES

TABLE 1

Steady-state metabolite labeling from $^{13}$C gluconate in *Y. lipolytica* lipogenic phase.

| | | $^{13}$C Gluconate + Acetate | | |
|---|---|---|---|---|
| | | Measured | Std. Error | Simulated |
| G6P | M + 0 | 63.2% | 0.3% | 64.4% |
| | M + 1 | 17.1% | 0.2% | 17.5% |
| | M + 2 | 7.9% | 0.2% | 6.9% |
| | M + 3 | 7.6% | 0.3% | 7.1% |
| | M + 4 | 2.2% | 0.2% | 2.1% |
| | M + 5 | 1.1% | 0.2% | 0.8% |
| | M + 6 | 1.0% | 0.2% | 1.3% |
| F6P | M + 0 | 64.4% | 0.3% | 64.5% |
| | M + 1 | 16.9% | 0.3% | 17.5% |
| | M + 2 | 7.3% | 0.3% | 6.9% |
| | M + 3 | 7.4% | 0.2% | 7.2% |
| | M + 4 | 2.1% | 0.2% | 2.1% |

TABLE 1-continued

Steady-state metabolite labeling from $^{13}C$ gluconate in *Y. lipolytica* lipogenic phase.

| | | $^{13}$C Gluconate + Acetate | | |
|---|---|---|---|---|
| | | Measured | Std. Error | Simulated |
| | M + 5 | 1.1% | 0.2% | 0.7% |
| | M + 6 | 0.9% | 0.2% | 1.1% |
| 3PG | M + 0 | 93.0% | 0.2% | 92.6% |
| | M + 1 | 1.5% | 0.2% | 1.6% |
| | M + 2 | 0.1% | 0.2% | 0.6% |
| | M + 3 | 5.5% | 0.2% | 5.2% |
| S7P | M + 0 | 53.6% | 0.2% | 53.6% |
| | M + 1 | 22.0% | 0.2% | 22.6% |
| | M + 2 | 9.7% | 0.2% | 9.7% |
| | M + 3 | 6.0% | 0.2% | 6.6% |
| | M + 4 | 3.6% | 0.2% | 3.7% |
| | M + 5 | 2.7% | 0.2% | 2.7% |
| | M + 6 | 1.2% | 0.2% | 0.8% |
| | M + 7 | 1.1% | 0.2% | 0.3% |
| 6PG | M + 0 | 63.7% | 0.3% | 62.6% |
| | M + 1 | 17.0% | 0.3% | 16.9% |
| | M + 2 | 6.6% | 0.3% | 6.5% |
| | M + 3 | 5.3% | 0.3% | 6.7% |
| | M + 4 | 1.6% | 0.3% | 2.0% |
| | M + 5 | 0.3% | 0.3% | 1.0% |
| | M + 6 | 5.5% | 0.3% | 4.3% |
| R5P | M + 0 | 66.9% | 0.2% | 67.2% |
| | M + 1 | 16.3% | 0.2% | 17.0% |
| | M + 2 | 7.1% | 0.3% | 4.8% |
| | M + 3 | 4.7% | 0.2% | 4.6% |
| | M + 4 | 1.5% | 0.3% | 2.0% |
| | M + 5 | 3.5% | 0.3% | 4.4% |
| PEP | M + 0 | 92.9% | 0.3% | 93.0% |
| | M + 1 | 1.2% | 0.2% | 1.5% |
| | M + 2 | 0.2% | 0.2% | 0.5% |
| | M + 3 | 5.7% | 0.3% | 5.0% |
| Pyr | M + 0 | 93.6% | 0.2% | 93.6% |
| | M + 1 | 1.2% | 0.2% | 1.4% |
| | M + 2 | 0.5% | 0.2% | 0.5% |
| | M + 3 | 4.7% | 0.2% | 4.6% |

G6P denotes glucose-6-phosphate;
F6P, fructose-6-phosphate;
3PG, 3-phosphoglycerate;
S7P, sedoheptulose-7-phosphate;
6PG, 6-phosphogluconate;
R5P, ribose-5-phosphate;
PEP, phosphoenolpyruvate.

The "Measured" column represents the experimental values measured by LC-MS while the "Simulated" column represents the simulation values that best fit the measured labeling, nutrient uptake, and product synthesis rates.

TABLE 2

Metabolic flux distributions of *Y. lipolytica* lipogenic phase with 95% confidence intervals (mmol gCDW$^{-1}$ hr$^{-1}$) determined by isotopomer balancing.

| | | | Gluconate + Acetate | | |
|---|---|---|---|---|---|
| Reaction | Substrates | Products | flux | L.B. | U.B. |
| Gluconate_IN | Gluconate | 6PG | 0.06 | 0.05 | 0.06 |
| PGI | G6P | F6P | −1.05 | −1.22 | −0.88 |
| PFK_FBPase | F6P | 1-BP | −0.39 | −0.69 | −0.07 |
| FBA | FBP | DHAP + GAP | −0.39 | −0.69 | −0.07 |
| TPI | DHAP | GAP | −0.37 | −0.42 | −0.32 |
| GAPDH | GAP | 13BPG | −0.32 | −0.36 | −0.27 |
| PGK | 13BPG | 3PG | −0.32 | −0.36 | −0.27 |
| PGM | 3PG | 2PG | −0.32 | −0.36 | −0.27 |
| ENO | 2PG | PEP | −0.32 | −0.36 | −0.27 |
| PYK | PEP | Pyr | −0.32 | −0.36 | −0.27 |
| G6PDH | G6P | 6PG | 0.62 | 0.46 | 0.80 |
| GND | 6PG | Ru5P + CO$_2$ | 1.05 | 0.88 | 1.22 |
| RPI | Ru5P | R5P | 1.10 | 0.93 | 1.28 |
| RPE | Ru5P | Xu5P | 0.37 | 0.31 | 0.43 |

TABLE 2-continued

Metabolic flux distributions of *Y. lipolytica* lipogenic phase with 95% confidence intervals (mmol gCDW$^{-1}$ hr$^{-1}$) determined by isotopomer balancing.

| | | | Gluconate + Acetate | | |
|---|---|---|---|---|---|
| Reaction | Substrates | Products | flux | L.B. | U.B. |
| TKT1 | R5P + Xu5P | S7P + GAP | 0.74 | 0.62 | 0.85 |
| TKT2 | E4P + Xu5P | F6P + GAP | 0.37 | 0.31 | 0.43 |
| TAL | S7P + GAP | E4P + F6P | 0.37 | 0.31 | 0.43 |
| SBA | DHAP + E4P | SBP | 0.29 | 0.00 | 0.58 |
| SBPase | SBP | S7P | −0.08 | −0.37 | 0.22 |
| PEP_IN | OA | PEP | 0.93 | 0.78 | 1.11 |
| PYR_IN | Mal | Pyr | 0.06 | 0.03 | 0.10 |
| Glyc3P_EX | DHAP | | 0.06 | 0.05 | 0.06 |
| Pyr_EX | Pyr | | 0.67 | 0.51 | 0.87 |

DHAP denotes dihydroxyacetone phosphate;
GAP, glyceraldehyde-3-phosphate;
13BPG, 1,3-bisphosphoglycerate;
SBP, sedoheptulose-1,7-bisphosphate;
Ru5P, ribulose-5-phosphate;
Xu5P, xylulose-5-phosphate;
E4P, erythrose-4-phosphate;
OA, oxaloacetate; and
Mal, malate.

L.B. and U.B. are the lower and upper bounds of 95% confidence intervals for the reaction fluxes.

TABLE 3

Steady-state metabolite labeling from $^{13}C$ glucose in *M. thermoacetica*.

| | | $^{13}$C Glucose + CO$_2$ | | |
|---|---|---|---|---|
| | | Measured | Std. Error | Simulated |
| 3PG | M + 0 | 3.1% | 0.5% | 3.2% |
| | M + 1 | 1.1% | 0.6% | 1.7% |
| | M + 2 | 12.2% | 2.1% | 10.7% |
| | M + 3 | 83.5% | 2.9% | 84.3% |
| PEP | M + 0 | 1.6% | 1.6% | 3.6% |
| | M + 1 | 0.9% | 0.9% | 1.9% |
| | M + 2 | 16.6% | 3.2% | 11.6% |
| | M + 3 | 80.9% | 5.0% | 82.9% |
| Ala | M + 0 | 34.7% | 1.0% | 33.8% |
| | M + 1 | 12.8% | 2.8% | 17.2% |
| | M + 2 | 32.3% | 1.5% | 31.5% |
| | M + 3 | 20.1% | 2.5% | 17.5% |
| Ser | M + 0 | 32.1% | 2.8% | 24.0% |
| | M + 1 | 10.8% | 2.3% | 18.9% |
| | M + 2 | 17.3% | 1.8% | 17.3% |
| | M + 3 | 39.7% | 1.0% | 39.8% |
| Gly | M + 0 | 39.0% | 2.9% | 43.7% |
| | M + 1 | 39.6% | 2.8% | 33.7% |
| | M + 2 | 21.4% | 4.7% | 22.6% |
| Glu | M + 0 | 7.9% | 1.1% | 4.7% |
| | M + 1 | 8.7% | 1.4% | 6.1% |
| | M + 2 | 36.6% | 0.6% | 39.3% |
| | M + 3 | 23.5% | 1.8% | 26.0% |
| | M + 4 | 22.9% | 1.4% | 23.4% |
| | M + 5 | 0.4% | 0.4% | 0.5% |
| Asp | M + 0 | 10.9% | 0.6% | 10.7% |
| | M + 1 | 5.2% | 0.5% | 6.0% |
| | M + 2 | 28.9% | 0.6% | 28.9% |
| | M + 3 | 54.1% | 1.4% | 53.2% |
| | M + 4 | 0.8% | 0.5% | 1.2% |
| cellular CO$_2$* | M + 0 | 96.6% | 1.6% | 97.7% |
| | M + 1 | 3.4% | 1.6% | 2.3% |
| acetyl-group* | M + 0 | 44.7% | 1.2% | 42.5% |
| | M + 1 | 24.0% | 3.0% | 20.6% |
| | M + 2 | 31.3% | 1.8% | 36.9% |

*Inferred from metabolite pairs with and without the moieties (acetyl-glutamate and glutamate, citrulline and ornithine).

TABLE 4

Metabolic flux distributions of *M. thermoacetica* with 95% confidence intervals (mmol gCDW$^{-1}$ hr$^{-1}$) determined by isotopomer balancing.

| | | | Glucose + CO$_2$ | | |
|---|---|---|---|---|---|
| Reaction | Substrates | Products | flux | L.B. | U.B. |
| GAPD_PGK | GAP | 3PG | 6.61 | 6.57 | 6.62 |
| PGM_ENO | 3PG | PEP | 6.56 | 4.07 | 6.58 |
| PYK | PEP | PYR | 7.02 | 0.00 | 7.60 |
| PPC | PEP | OA | −0.46 | −1.05 | 6.53 |
| PC | PYR | OA | 0.72 | −6.28 | 1.31 |
| PFOR | PYR | AcCoA + CO$_2$ | 6.19 | 3.76 | 6.25 |
| CS | AcCoA + OA | Cit | 0.10 | 0.08 | 0.10 |
| ACON_IDH | Cit | aKG + CO$_2$ | 0.10 | 0.08 | 0.10 |
| AKGD | aKG | SuccCoA + CO$_2$ | 0.00 | 0.00 | 0.00 |
| PHGDH | 3PG | Ser | 0.05 | 0.00 | 2.54 |
| SHMT | Ser | Gly + MLTHF | 0.02 | −0.03 | 2.52 |
| GCS_a | Gly | Gly—CO$_2$* + CO$_2$ | −0.03 | −0.09 | 2.46 |
| GCS_b | Gly—CO$_2$* | MLTHF | −0.03 | −0.09 | 2.46 |
| FDH_FTHL | CO$_2$ | FTHF | 3.57 | −0.75 | 3.68 |
| MTHFC_MTHFD | FTHF | MLTHF | 3.57 | −0.75 | 3.68 |
| MTHFR | MLTHF | MTHF | 3.57 | 1.76 | 5.29 |
| MTRCFSP | MTHF | MCFeSP | 3.57 | 1.76 | 5.29 |
| CODH_ACS | MCFeSP + CO$_2$ | AcCoA | 3.57 | 1.76 | 5.29 |
| ACCOA_EX | AcCoA | | 9.66 | 7.91 | 9.67 |
| ALA_EX | Pyr | | 0.10 | 0.08 | 0.10 |
| ASP_EX | OA | | 0.17 | 0.14 | 0.17 |
| GLU_EX | aKG | | 0.10 | 0.08 | 0.10 |
| GLY_EX | Gly | | 0.05 | 0.05 | 0.06 |
| SER_EX | Ser | | 0.03 | 0.03 | 0.03 |

MCFeSP denotes methylcorrinoid iron-sulfur protein;
ML, methylene;
MLTHF, methylene-THF;
FTHF, formyl-THF; and
MTHF, methyl-THF.
L.B. and U.B. are the lower and upper bounds of 95% confidence intervals for the fluxes.
*' ' sign indicates transition state in which the molecule that follows the sign is cleaved from the substrate that precedes the sign.

TABLE 5

Acetate yields, productivities, and CO$_2$ fixation rates with varying energy sources in *M. thermoacetica*.

| Condition | Glucose feed concentration (g/L) | Dilution rate (hr$^{-1}$) | Gas and Pressure (kPa) | Fraction of e$^-$ from glucose | Acetate yield (g ace/g glc) | Acetate productivity (mmol gCDW$^{-1}$ hr$^{-1}$) | CO2 fixation rate (mmol gCDW$^{-1}$ hr$^{-1}$) |
|---|---|---|---|---|---|---|---|
| Batch | n/a | n/a | CO$_2$; 170 | 100% | 0.77 ± 0.02 | 8.0 ± 0.1 | −1.5 ± 0.5 |
| Batch | n/a | n/a | 80:20 H$_2$/CO$_2$; 240 | 24.9 ± 1.4% | 3.8 ± 0.2 | 23.3 ± 0.8 | 36.6 ± 1.7 |
| Batch | n/a | n/a | 80:20 H$_2$/CO$_2$; 240 | 12.4 ± 1.1% | 7.5 ± 0.6 | 26.6 ± 0.9 | 50.0 ± 1.9 |
| Chemostat | 0.25 | 0.017 | 60:40 H$_2$/CO$_2$; 130 | 2.9 ± 0.1% | 33.4 ± 1.3 | 11.1 ± 0.3 | 22.3 ± 0.7 |
| Chemostat | 0.25 | 0.009 | 60:40 H$_2$/CO$_2$; 130 | 1.9 ± 0.1% | 52.3 ± 2.9 | 9.2 ± 0.2 | 18.3 ± 0.5 |
| Chemostat | 0.13 | 0.009 | 60:40 H$_2$/CO$_2$; 130 | 1.2 ± 0.1% | 82.1 ± 7.2 | 6.9 ± 0.4 | 13.9 ± 0.8 |

TABLE 6

New reactions and genes added to the *M. thermoacetica* metabolic model iAI563.

| Reaction Abbreviation | Reaction Name | Reaction Formula | Genes Associated with Reactions | Model Subsystem |
|---|---|---|---|---|
| ALCD2x | Alcohol dehydrogenase (ethanol) | etoh[c] + nad[c] <=> acald[c] + h[c] + nadh[c] | ( Moth_1024 and Moth_1911 and Moth_2268 ) | Alternate Carbon Metabolism |
| ALCD2yi | Alcohol dehydrogenase (ethanol, NADP) | acald[c] + h[c] + nadph[c] -> etoh[c] + nadp[c] | ( Moth_1024 and Moth_1911 and Moth_2268 ) | Alternate Carbon Metabolism |
| ACALD | Acetaldehyde dehydrogenase (acetylating) | acald[c] + coa[c] + nad[c] <=> accoa[c] + h[c] + nadh[c] | Moth_1776 | Central Metabolism |
| AOR_MT | Acetaldehyde:ferredoxin oxidoreductase | ac[c] + fdxrd[c] + 3 h[c] -> acald[c] + fdxox[c] + h2o[c] | Moth_0722 | Central Metabolism |
| EX_etoh(e) | Ethanol exchange | etoh[e] <=> | | Exchange |
| ETOHt | Ethanol reversible transport | etoh[e] <=> etoh[c] | | Transport |

TABLE 7

Corrected reactions in the *M. thermoacetica* metabolic model iAI563.

| Reaction Abbreviation | Reaction Name | Published Model iAI558 | Updated Model iAI563 |
|---|---|---|---|
| FRHD | Hydrogenase (ferredoxin) | 2 fdxrd[c] + 3 h[c] <=> 2 fdxox[c] + h2[c] + h[e] | fdxrd[c] + 3 h[c] <=> fdxox[c] + h2[c] + h[e] |
| CODH | Carbonmonoxide dehydrogenase (ferredoxin) | co[c] + 2 fdxox[c] + h2o[c] -> co2[c] + 2 fdxrd[c] + 2 h[c] | co[c] + fdxox[c] + h2o[c] -> co2[c] + fdxrd[c] + 2 h[c] |
| PFOR | Pyruvate ferredoxin oxidoreductase | 2 fdxrd[c] + 2 h[c] + co2[c] + accoa[c] <=> 2 fdxox[c] + pyr[c] + coa[c] | fdxrd[c] + 2 h[c] + co2[c] + accoa[c] <=> fdxox[c] + pyr[c] + coa[c] |
| HYDFDNr | Electron bifurcating Ferredoxin:NAD hydrogenase (HydABC) | 2 fdxox[c] + 2 h2[c] + nad[c] <=> 2 fdxrd[c] + 3 h[c] + nadh[c] | fdxox[c] + 2 h2[c] + nad[c] <=> fdxrd[c] + 3 h[c] + nadh[c] |

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for converting carbon dioxide into organic compounds, comprising:
    culturing non-photosynthetic autotrophic cells in a culture vessel containing a fermentation medium comprising:

a controlled, limiting amount of a first preferentially utilized carbon substrate, a controlled amount of carbon dioxide ($CO_2$), and a controlled amount of diatomic hydrogen ($H_2$), wherein the controlled, limiting amount of the first preferentially utilized carbon substrate is added to the culture vessel at a rate such that the culture vessel maintains a concentration of the first preferentially utilized carbon substrate such that the $CO_2$, which is not preferentially utilized by the cells, provides more than 50% of carbon in organic compounds produced by the cells, optionally wherein the non-photosynthetic autotrophic cells are acetogenic cells; and wherein the limiting amount of the first preferentially utilized carbon substrate is an amount that provides less than 25% of the quantity of electrons in the culture.

2. The method of claim 1, wherein the first preferentially utilized carbon substrate comprises one or more sugars.

3. The method of claim 1, wherein the limiting amount of the first preferentially utilized carbon substrate is an amount that provides less than about 20%, less than about 15%, less than about 10%, less than about 5%, less than about 2%, or less than about 1% of the quantity of electrons in the culture.

4. The method of claim 1, wherein the quantity of electrons provided by $H_2$ is at least about 75%, at least about 80%, at least about 85%, at least about 90%, at least about 95%, at least about 98%, or at least about 99% of the quantity of electrons in the culture.

5. The method of claim 1, wherein the acetogenic cells comprise *Moorella thermoacetica*, *Clostridium ljungdahlii*, or *Acetobacterium woodii*.

6. The method of claim 1, wherein the controlled, limiting amount of the first preferentially utilized carbon substrate is added to the culture vessel at a rate such that the culture vessel maintains a concentration of the first preferentially utilized carbon substrate such that catabolite repression is not induced.

7. A method for converting carbon dioxide into lipids comprising:
(a) culturing non-photosynthetic autotrophic cells according to the method of claim 1 to produce acetate, and
(b) culturing oleaginous cells in a culture vessel containing a fermentation medium comprising: a controlled, limiting amount of a second preferentially utilized carbon substrate, and the acetate produced in (a) to produce lipids, wherein the second preferentially utilized carbon substrate is added to the culture vessel at a rate such that the culture vessel maintains a concentration of the second preferentially utilized carbon substrate such that the acetate, which is not preferentially utilized by the cells, provides the majority of carbon for organic compounds produced by the cells, optionally wherein the oleaginous cells are oleaginous yeast cells;

wherein the second preferentially utilized carbon substrate of (b) provides NADPH and/or another cofactor with reducing capabilities to the cells of (b), optionally wherein the cofactor with reducing capabilities is a ferredoxin, NADH, and/or FADH2; and/or wherein the second preferentially utilized carbon substrate of (b) provides ATP and/or another cofactor with high-energy phosphate bond(s) to the cells of (b), optionally wherein the cofactor with high-energy phosphate bond(s) is GTP and/or pyrophosphate.

8. The method of claim 7, wherein the oleaginous cells overexpress a kinase that phosphorylates the second preferentially utilized carbon substrate.

9. The method of claim 7, wherein the amount of the second preferentially utilized carbon substrate is sufficient to generate reduced nicotinamide adenine dinucleotide phosphate (NADPH) through the oxidative pentose phosphate pathway (oxPPP) and convert acetyl-CoA into lipids, but is insufficient to be incorporated into the lipids as a major component.

10. The method of claim 7, wherein the initial supplied concentration of acetate is at least 34 grams per liter.

11. The method of claim 7, wherein the second preferentially utilized carbon substrate is one or more of gluconate, glycerol, and/or a hexose, optionally glucose or fructose.

12. The method of claim 7, wherein the acetate provides acetyl-CoA and ATP necessary for converting acetyl-CoA into lipids.

13. The method of claim 7, wherein the controlled, limiting amount of the second preferentially utilized carbon substrate is added to the culture vessel at a rate such that the culture vessel maintains a concentration of the second preferentially utilized carbon substrate such that catabolite repression is not induced.

14. A method of producing bioproducts comprising
(a) culturing non-photosynthetic autotrophic cells according to the method of claim 1 to produce acetate, and
(b) culturing cells that utilize acetate to produce bioproducts in a culture vessel containing a fermentation medium comprising: a controlled, limiting amount of a second preferentially utilized carbon substrate utilized by the cells that utilize acetate, and the acetate produced in (a) to produce the bioproducts, wherein the second preferentially utilized carbon substrate utilized by the cells that utilize acetate is added to the culture vessel at a rate such that the culture vessel maintains a concentration of the second preferentially utilized carbon substrate utilized by the cells that utilize acetate such that the acetate, which is not preferentially utilized by the cells, provides the majority of carbon for organic compounds produced by the cells;

wherein the second preferentially utilized carbon substrate of (b) provides NADPH and/or another cofactor with reducing capabilities to the cells, optionally wherein the cofactor with reducing capabilities is a ferredoxin, NADH, and/or FADH2; and/or wherein the second preferentially utilized carbon substrate of (b) provides ATP and/or another cofactor with high-energy phosphate bond(s) to the cells, optionally wherein the cofactor with high-energy phosphate bond(s) is GTP and/or pyrophosphate.

15. The method of claim 14, wherein the bioproducts are oleochemicals, polyketides, or mevalonate pathway derived natural products.

16. The method of claim 15, wherein the mevalonate pathway derived natural products are terpenoids or derivatives thereof.

17. The method of claim 14, wherein the second preferentially utilized carbon substrate is one or more of gluconate, glycerol, and/or a hexose, optionally glucose or fructose.

18. The method of claim 14, wherein the controlled, limiting amount of the second preferentially utilized carbon substrate is added to the culture vessel at a rate such that the culture vessel maintains a concentration of the second preferentially utilized carbon substrate such that catabolite repression is not induced.

* * * * *